US007098303B1

(12) United States Patent
Weiner et al.

(10) Patent No.: US 7,098,303 B1
(45) Date of Patent: Aug. 29, 2006

(54) CONSERVED MOTIF OF HEPATITIS C VIRUS E2/NS1 REGION

(75) Inventors: Amy J. Weiner, Benicia, CA (US); Michael Houghton, Danville, CA (US)

(73) Assignee: Novartis Vaccines and Diagnostics, Inc., Emeryville, CA (US)

(*) Notice: Subject to any disclaimer, the term of this patent is extended or adjusted under 35 U.S.C. 154(b) by 0 days.

(21) Appl. No.: 08/437,952

(22) Filed: May 9, 1995

Related U.S. Application Data

(62) Division of application No. 08/061,699, filed on May 12, 1993, now abandoned.

(51) Int. Cl.
*C07K 14/18* (2006.01)
*A61K 39/29* (2006.01)

(52) U.S. Cl. .................. 530/324; 530/806; 530/826; 530/329; 530/300; 530/350; 530/403; 424/189.1; 424/228.1; 424/185.1; 424/186.1; 424/192.1; 424/193.1; 424/196.11; 424/197.11; 424/201.1; 424/204.1; 424/238.1; 514/2; 514/12

(58) Field of Classification Search ............ 424/189.1, 424/228.1, 185.1, 186.1, 192.1, 193.1, 196.11, 424/197.11, 201.1, 204.1, 238.1; 530/329, 530/300, 826, 324, 325, 326, 327, 328, 806, 530/403, 350; 514/2, 12
See application file for complete search history.

(56) References Cited

U.S. PATENT DOCUMENTS

| | | | |
|---|---|---|---|
| 4,341,761 A | 7/1982 | Ganfield et al. | 424/85 |
| 4,399,121 A | 8/1983 | Albarella et al. | 260/112.5 R |
| 4,427,783 A | 1/1984 | Newman et al. | 436/542 |
| 4,444,887 A | 4/1984 | Hoffmann | 435/240 |
| 4,466,917 A | 8/1984 | Nussenzweig et al. | 260/112 R |
| 4,472,500 A | 9/1984 | Milstein et al. | 435/68 |
| 4,491,632 A | 1/1985 | Wands et al. | 435/240 |
| 4,493,890 A | 1/1985 | Morris | 435/7 |
| 4,517,304 A | 5/1985 | Stott et al. | |
| 4,629,783 A | 12/1986 | Cosand | 530/324 |
| 4,683,195 A | 7/1987 | Mullis et al. | 435/6 |
| 4,683,202 A | 7/1987 | Mullis | 435/91 |
| 4,722,840 A | 2/1988 | Valenzuela et al. | 424/88 |
| 4,816,397 A | 3/1989 | Boss et al. | 435/68 |
| 4,816,567 A | 3/1989 | Cabilly et al. | 530/387 |
| 5,308,750 A | 5/1994 | Melita et al. | |
| 5,574,132 A * | 11/1996 | Lacroix | 530/323 |
| 5,728,520 A | 3/1998 | Weiner et al. | |
| 5,747,239 A * | 5/1998 | Wang et al. | 435/5 |
| 5,756,312 A | 5/1998 | Weiner et al. | |
| 5,766,845 A | 6/1998 | Weiner et al. | |
| 5,942,234 A * | 8/1999 | Ralston et al. | 424/228.1 |
| 6,146,633 A | 11/2000 | Stevens | |

FOREIGN PATENT DOCUMENTS

| | | |
|---|---|---|
| EP | 0 116 201 A1 | 8/1984 |
| EP | 0 120 551 A2 | 10/1984 |
| EP | 0 164 556 A2 | 12/1985 |
| EP | 0 259 149 A2 | 3/1988 |
| EP | 0 360 088 A2 | 3/1990 |
| EP | 0 388 232 A1 | 9/1990 |
| EP | 0 468 527 A2 | 1/1992 |
| EP | 0 725 824 B1 | 8/1996 |
| EP | 0 759 937 B1 | 3/1997 |
| WO | WO 89/04669 | 6/1989 |
| WO | 9011089 * | 10/1990 |
| WO | WO 90/14436 | 11/1990 |
| WO | WO 90/14837 | 12/1990 |
| WO | WO 92/08734 | 5/1992 |
| WO | WO 93/00365 | 1/1993 |
| WO | WO 93/04205 | 4/1993 |
| WO | WO 93/06126 | 4/1993 |
| WO | WO 93/16126 | 8/1993 |
| WO | WO 93/18054 | 9/1993 |

OTHER PUBLICATIONS

Weiner et al., PNAS, 89: 3468-3472, 1992.*
Choo et al., PNAS USA, 91: 1294-1298, 1994.*
Seauer, Gen. Eng. News, 14: 10 and 21, 1994.*
Berzofsky et al., "Chapter 8", from "Fundamentals of Immunology. Second Ed." Ed. W. E. Paul, Raven Press, 1989, pp. 176, 177, 201, 202.*
Taniguchi et al., Virol., 195: 297-301, 1993.*
Barrett, J.T., *Basic immunology and its medical application*, Second Edition, 1980, 14-17.
Botarelli, P. et al., "T-Lymphocyte Response to Hepatitis C Virus in Different Clinical Courses of Infection", *Gastroenterology*, 1993,104, 580-587.
Brennan, M. et al., "The folicle cells are a major site of vitellogenin in *Drosophila melanogaster*", *Dev. Biol.*, 1982, 89, 225-236.
Broach, R., "Construction of High Copy Yeast Vectors Using 2-μm Circle Sequences," *Meth. Enz.*, 1983, 101, 307-325.
Cha et al., "At least five related, but distinct, hepatitis C viral genotypes exist," *Proc. Natl. Acad. Sci USA*, 1992, 89, 7144-7148.

(Continued)

Primary Examiner—Ronald B. Schwadron
(74) Attorney, Agent, or Firm—Roberta L. Robins; Michael J. Moran; Alisa A. Harbin

(57) ABSTRACT

Immunogenic polypeptides comprising hepatitis C virus (HCV) immunogens are described. The HCV immunogen comprises the amino acid sequence Xaa-Thr-Xaa-Val-Thr-Gly-Gly-Xaa-Ala-Ala-Arg-Thr-Thr-Xaa-Gly-Xaa-Xaa-Ser-Leu-Phe-Xaa-Xaa-Gly-Xaa-Ser-Gln-Xaa-Ile-Gln-Leu-Ile (SEQ ID NO:8). The immunogenic polypeptide can be coupled to a bacterial toxoid, such as a diphtheria toxoid.

4 Claims, 8 Drawing Sheets

OTHER PUBLICATIONS

Chakrabarti et al., "Vaccinia Virus Expression Vector: Coexpression of β-Galactosidase Provides Visual Screening of Recombinant Virus Plaques," *Mol. Cell Biol.*, 1985, 5(12), 3403-3409.

Chan et al., "Analysis of a new hepatitis C virus type and its phylogenetic relationship to existing variants," *J. Gen. Virol.*, 1992, 73, 1131-1141.

Choo, Q.L. et al., "Genetic organization and diversity of the hepatitis C virus", *Proc. Natl. Acad. Sci. USA*, 1991, 88, 2451-2455.

Choo, Q.L. et al., "Hepatitis C virus: The major causative agent of viral non-A, non-B hepatitis", *Br. Med. Bull.*, 1990, 46(2); 423-441.

Choo, Q.L. et al., "Hepatitis C virus is a distant relative of the flaviviruses and pestiviruses", in *Proceedings of the International Meeting on Non-A, Non-B Hepatitis*, Shikata, T. et al. (eds.), Tokyo, Japan, Amsterdam: Elsevier, 1991, 47-52.

Choo, Q.L. et al., "Isolation of a cDNA clone derived from a blood-borne non-A, non-B viral hepatitis genome", *Science*, 1989, 244, 359-362.

Choo, Q.L. et al., "Identification of the major, parenteral non-A, non-B hepatitis agent (hepatitis C virus) using a recombinant cDNA approach", *Seminars in Liver Disease*, 1992 12(3), 279-288.

Cofin et al. (eds.), *RNA Tumor Viruses*, 2nd Edition, Cold Spring Harbor Laboratory, New York, 1985, vol. 2, 17-73.

Cuypers, H.T. et al., "Storage conditions of blood samples and primer selection affect the yield of cDNA polymerase chain reaction products of hepatitis C virus", *J. Clin. Microbiol.*, 1992, 30(12), 3220-3224.

Cuypers, H.T.M. et al., "Analysis of genomic variability of hepatitis-C virus", *J. Hepatology*, 1991, 13(Suppl. 4), S15-S19.

DeBoer et al., "The tac promotor: a functional hybrid derived from the trp and lac promoters," *Proc. Natl. Acad. Sci. USA*, 1983, 80(1), 21-25.

Erickson, A.L. et al., "Hepatitis C virus-specific CTL responses in the liver of chimpanzees with acute and chronic hepatitis C", *J. Immunol.*, 1993, 151(8), 4189-4199.

Fausto-Sterling, A. et al., "Analysis of a newly-isolated temperature-sensitive maternal-effect mutation of *Drosophila melanogaster*", *J. Exper. Zoo.*, 1976, 200, 199-209.

Fiers et al., "Complete nucleotide sequence of SV40 DNA," *Nature*, 1978, 273, 113-120.

Goeddel et al., "Synthesis of human fibroblast interferon by *E. coli*," *Nucl. Acids Res.*, 1980, 8(18), 4057-4075.

Guntaka R.V. et al., "Effect of 5-Methyllcytidine on virus production in avian sarcoma virus-infected chicken embryo cells", *Virology*, 1979, 29(2), 475-482.

Guntaka, R.V. et al., "Effect of dibutyrlcyclic AMP on intracellular levels of avian sarcoma virus specific RNA", *Nature*, 1978, 274, 274-276.

Hess et al., "Cooperation of glycolytic enzymes," *J. Adv. Enzyme Reg.*, 1968, 7, 149-167.

Hitzeman et al., "Isolation and Characterization of the Yeast 3-Phosphoglycerokinase Gene (PGK) by an Immunological Screening Technique," *J. Biol. Chem.*, 1980, 255(24), 12073-12080.

Holland et al., "The primary structures of two yeast enolase genes," *J. Biol. Chem.*, 1981, 256(3), 1385-1395.

Holland et al., "Isolation and identification of yeast messenger ribonucleic acids coding for enolase, glyceraldehyde-3-phosphate dehydrogenase, and phosphoglycerate kinase," *Biochem.*, 1978 17(23), 4900-4907.

Houghton, M. et al., "The hepatitis C virus: Genetic organization, persistence, and vaccine strategies," in *Viral Hepatitis and Liver Disease*, Nishioka, K. et al. (eds.), Springer-Verlag, Tokyo, 1994, 33-37.

Houghton, M. et al., "Hepatitis C virus: Structure, protein products and processing of the polyprotein precursor", *Curr. Stud. Hematol. Blood Transfus. (Switzerlaned)*, 1994, 61, 1-11.

Houghton, M. et al., "Hepatitis delta (δ) virus (HDV): Its relationship with introns and plant viroid-like agents and the mapping of immunogenic epitopes within viral polypeptides", *J. Med. Virol.*, 1987, 21(4) 37A, Abstract 106.

Houghton et al., "Molecular biology of the hepatitis C viruses: implications for diagnosis, development and control of viral disease," *Hepatology*, 1991, 14(2), 381-388.

Jansen et al, "Immunotoxins: Hybrid Molecules Combining High Specificity and Potent Cytotoxicity," *Immun. Rev.*, 1982, 62, 185-216.

Jones et al., "The use of maleimidocaproyloxysuccinimide to prepare malarial peptide carrier immunogens," *J. Immunol. Methods*, 1989, 123, 211-216.

Kato et al., "Distribution of plural HCV types in Japan," *Biochem. Biophys. Res. Commun.*, 1991, 181(1), 279-285.

Kubo, Y. et al. "A cDNA fragment of hepatitis C virus isolated from an implicated donor of post-transfusion non-A, non-B hepatitis in Japan", *Nucl. Acids Res.*, 1989, 17(24), 10367-10372.

Lee et al., "A method for preparing β-hCG cooh peptide-carrier conjugates of predictable composition," *Mol. Immunol.*, 1980, 17, 749-756.

Luckow et al., "High level expression of nonfused foreign genes with *Autographa californica* nuclear polyhedrosis virus expression vectors," *Virology*, 1989, 170, 31-39.

Mackett et al., "General method for production and selection of infectious vaccinia virus recombinants expressing foreign genes," *J. Virol.*, 1984, 49(3), 857-864.

Martell, M. et al., "Hepatitis C virus (HCV) circulates as a population of different but closely related genomes: Quasispecies nature HCV genome distribution", *J. Virol.*, 1992, 66(5), 3225-3229.

Mori et al., "A new type of hepatitis C virus in patients in thailand," *Biochem. Biophys. Res. Commun.*, 1992, 183(1), 334-342.

Moss, "Vaccinia virus expression vectors," *Gene Transfer Vectors for Mammalian Cells*, Miller et al. (eds.), Cold Spring Harbor Laboratory, Cold Spring Harbor, N. Y., 1987, 10-14.

Ogata et al., "Nucleotide sequence and mutation rate of the H strain of hepatitis C virus," *Proc. Natl. Acad. Sci. USA*, 1991, 88, 3392-3396.

Okamoto et al., "Full-length sequence of a hepatitis C virus genome having poor homology to reported isolates: Comparative study of four distinct genotypes," *Virology*, 1992, 188, 331-341.

Partis et al., "Cross-linking of protein by ω-maleimido alkanoyl *N*-hydroxysuccinimido esters," *Prot. Chem.*, 1983, 2(3), 263-277.

Pearson et al., Improved tools for biological sequence comparison, *Proc. Natl. Acad. Sci. USA*, 1988, 85, 2444-2448.

Peeters et al., "Comparison of four bifunctional reagents for coupling peptides to proteins and the effect of the three moieties on the immunogenicity of the conjugates," *J. Immunol. Methods*, 1989, 120, 133-143.

Saiki et al., "Analysis of enzymatically amplified β-globin and HLA-DQα DNA with allele-specific oligonucleotide probes," *Nature*, 1986, 324, 163-166.

Saracco, G. et al., "Long-term follow-up of patients with chronic hepatitis C treated with different doses of Interferon-$a_{2b}$", *Hepatology*, 1993, 18(6), 1300-1305.

Scharf et al., "Direct cloning and sequence analysis of enzymatically amplified genomic sequences," *Science*, 1986, 233, 1076-1078.

Scott, M.P. et al., "Structural relationships among genes that control development: sequence homology between the antennapedia, ultrabithorax and fushi tarazu loci of *Drosophila*", *PNAS*, 1984, 81, 4115-4119.

Scott, M.P. et al., "The molecular organization of the *Antennapedia* complex in *Drosophila melanogaster*", *Cell*, 1983, 35, 763-766.

Shimatake et al., "Purified λ regulatory protein cII positively activates promoters for lysogenic development," *Nature*, 1981, 292, 128-132.

Shimizu, Y.K. et al., "Early events in hepatitis C virus infection of chimpanzees", *Proc. Natl. Acad. Sci. USA*, 1990, 87, 6441-6444.

Simmonds, P. et al., "A proposed system for the nomenclature of hepatitis C viral genotypes", *Hepatology*, 1994, 19, 1321-1324.

Smith et al., "Production of Human Beta Interferon in Insect Cell Infected with a Baculovirus Expression Vector," *Mol. Cell Biol.*, 1983, 3(12), 2156-2165.

Summers et al., "A Manual of Methods for Baculovirus Vectors and Insect Cell Culture Procedures," Texas Agricultural Experiment Station Bulletin No. 1555, 1987, 1-56.

van der Poel, C.L. et al., "Confirmation of hepatitis C virus infection by new four-antigen recombinant immunoblot assay", *Lancet*, 1990, 337, 317-319.

Wang, K.S. et al., "The viroid-like structure of the hepatitis delta (δ) genome: synthesis of a viral antigen in recombinant bacteria," *The Hepatitis Delta Virus and Its Infection*, Rizzetto, M. et al. (eds.), 1987, vol. 24, 71-82.

Wang, K.S. et al., "Structure, sequence and expression of the hepatitis delta (d) viral genome", *Nature*, 1986, 323, 508-514.

Weiner et al., "Variable and hypervariable domains are found in the regions of HCV corresponding to the flavivirus envelope and NS1 proteins and the pestivirus envelope glycoproteins," *Virology*, 1991, 180, 842-848.

Weiner et al., "The Hypervariable Amino Terminus of the Hepatitis C Virus E2/NS1 Protein Appears to be Under Immune Selection," *Vaccines*, 1992, 92, 303-308.

Weiner, A.J. t al., "Detection of hepatitis C viral sequences in non-A, non-B hepatitis", *Lancet*, 1990, 335, 1-3.

Weiner, A.J. et al., "Hepatitis delta (δ) cDNA clones: undetectable hybridization to nucleic acids from infectious non-A, non-B hepatitis materials and hepatitis B DNA", *J. Med. Virol.*, 1987, 21, 239-247.

Weiner, A.J. et al., "Application to Polymerase Chain Reaction to Hepatitis C Virus Research and Diagnostics", in *Diagnosis of Human Viruses by Polymerase Chain Reaction Technology*, Becker, Y. et al. (eds.), Springer Verlag, New York, 1992, Ch.8, 86-100.

Weiner, A.J. et al., "A molecular analysis of the *fushi tarazu*, a gene in *Drosophila melanogaster* that encodes a product affecting embryonic segment number and cell fate", *Cell*, 1984, 37, 843-851.

Weiner, A.J. et al., "Sequence variation in hepatitis C viral isolates", *J. Hepatology*, 1991, 13 (Suppl. 4), S6-S14.

Weiner, A.J. et al., "A Unique, Predominant Hepatitis C Virus Variant Found in an Infant Born to a mother with multiple variants", *J. Virol.*, 1993, 67(7), 4365-4368.

Weiner, A.J. et al., "A single antigenomic open reading frame of the hepatitis delta virus encodes the epitope(s) of both hepatitis delta antigen polypeptides $p24^\delta$ and $p27^\delta$ ", *J. Virol.*, 1988, 62(2), 594-599.

Weiner, A.J. et al., "HCV-positive, HIV-1-negative mothers transmit HCV," in *Viral Hepatitis and Liver Disease*, Nishioka, K. et al. (eds.), Springer-Verlag, Tokyo, 1994, 463-467.

Weiner, A.J. et al., "HCV testing in a low-risk population", *Lancet*, 1990, 336, 695.

Weiner, A. et al., "Persistent hepatitis C virus infection in a chimpanzee is associated with emergence of a cytotoxin T lymphocyte escape variant", *Proc. Natl. Acad. Sci. USA*, 1995, 92, 2755-2759.

Weiner, A., "Humoral response to linear B cell epitopes in the amino terminus of the hepatitis C virus envelope glycoprotein gp72 (E2): Role in protective immunity still unknown", *Hepatology*, 1995, 22(1), 369-371.

Esquivel et al., "T Cell Recognition of Hepatitis C Virus in Patients wituh Chronic Hepatitis C," Gastroenterology, vol. 104, No. 4, Part 2, Apr. 1993, one page.

Esumi et al., Vaccine, vol. 20, 2002 (abstract), pp. 3095-3103.

Fahey et al., Clin Exp. Immunol., (1992) 88:1-5.

Farci et al., "Prevention of Hepatitis C Virus Infection in Chimpanzees by Hyperimmune Serum Against the Hypervariable Region 1 of Envelope 2 Protein," PNAS 1996, 93(26):15394-9.

Hattori et al., "Cross-Reactivity of Anti-Hypervariable Region Antibody of HCV Infected Patients," 4th Internat'l Meeting on Hepatitis C Virus and Related Viruses, Mar. 6-10, 1997, Kyoto, Japan, p. 119 and abstract p. 306.

Hijikata et al., 1991 Biochemical and Biophysical Research Communications 175(1):220-228.

Lesniewski et al., *Chemical Abstracts*, (1993) 119: 1353580, p. 488.

Rudinger, in *Peptide Hormones*, ed. J.A. Parsons, University Park Press, Baltimore (1976). pp. 1-7.

\* cited by examiner

```
Consensus            .T.VTGG.AARTT.G..SLF..G.SQ.IQLI    31
re3       (15-45)    A.YA..AAQGHA.NSFV...RS.A..NLK.V    45
hcj7.pep  (15-45)    S.Q.....Q..H.VR.VA.I.SP.SR.D.S..   45
ny1.pep   (15-45)    S.R.....QQG.AVH.IA...SL.A..K...V   45
GE11.2    (15-45)    S.H.M.AQQG.VAK.FT...GP.PA.K....    45
s71957.p  (15-45)    S.H..AVQGHSIR.LT...TS.PA.K...V     45
ec10      (15-45)    E.H....I..K..ASLTG..NL.AK.N....    45
sp2.tc    (15-45)    E.H....N.G.AAA.IAG...TL.AK.NV...   45
M2.2      (15-45)    Q.R....T..QS.ARIAG...SL.AR.N....   45
rela      (15-45)    Q.H.M..T.G.NAY.LT.FLSV.A..K....    45
168       (15-45)    E.H.M..A.SS..YRFA....TS.PA.K...V   45
M1.5      (15-45)    E.H....S...S..ATFSK..MP.A..N....   45
hpcprc1a.p1 (14-44)  G.TRV..A.....SSFA..LTH.P..N....V   44
gm2.tc    (15-45)    G.H....A...DAFRFS...TR.P..N....    45
s71864.p1 (15-45)    A.NM...AP....YKLTT...SY.A..K....   45
i15.tc    (15-45)    HNH....TS..N.F.ITT...TQ.P..KL..V   45
sp1.tc    (15-45)    G.H....A...NAHSLT..LAP.A..K....    45
re37b     (15-45)    T.R.S..T..H..A.LT...SP.PR.N.H.V    45
re39      (15-45)    T.H.S..T.G...ASLT.F.AP.A..R...V    45
hpchcj2.p (15-45)    T.H....ATGH..S.IA...LP.A..K....    45
hpccgenom.p1 (15-45) D.YAS..AQG.S.L.FT...TP.A..K....    45
hpcprc4a.p2 (14-44)  D.YAS..A.G.A.Y.IT...AP.A..N....    44
hpcprc11a.p1 (4-34)  R.YAS..A.G...H.FT...ST.AR.N....    34
re72b     (15-45)    Q.Y...K..Q.VS.FTG...SS.P..K....    45
hpcprc3a.p1 (4-34)   D.Y.S..A...SIS.FT...TP.A..K...V    34
re70      (15-45)    S.Y....E.S...R.FA...TL.S..K....    45
re42      (15-45)    N.Y....S.G.AVA.FAG.LQP.AK.NV...    45
63        (15-45)    H.R....QV.FR.H.LV....TQ.P..K...V   45
hcvj      (15-45)    H.H....RV.SS.QSLV.WLSQ.P..K...V    45
hcvj1     (15-45)    H.R....VQGHV.STLT...RP.A..K...V    45
re38      (15-45)    H.R....VQG.D.S.LV...SL.P..K...V    45
bk        (15-45)    N.R....VQG.D.S.LV...SL.P..K...V    45
re5       (15-45)    D.H....AQ.K..NRLV.M.AS.P..K....    45
re35      (15-45)    E.H....AS....QRFT.F.DL.P..K...V    45
re36      (15-45)    T.YM...AN....Q.FV...TP.PA.K...V    45
re54      (15-45)    E.H....TS....Q.FV...SA.A..K...V    45
re56      (15-45)    G.H....Q.....QSFT...SP.PQ.K....    45
64        (15-45)    R.H....K..H..K.FA...TP.P..N....    45
re62      (15-45)    E.R....AVQGHGAL.LA...TP.P..K....   45
re41      (15-45)    E.R....AI.G..ASSFAG..TS.A..K...V   45
hpcvjk3.p (15-45)    E.R....QQVG...QSLT...TP.P..T....   45
jk2       (15-45)    Q.R....AQVG...SSLT...TP.P..N...V   45
hcv1      (15-45)    R.Q....AQ.GH..S.LA...TP.P..K...V   45
us5.tc    (15-45)    E.H....S.GH.VS.FV...LAP.AK.NV...   45
                     E.H....S.GH.VT.IA...TS.AK.N....    45
```

FIG. 2A

```
i21.tc      (15-45)    S.H....T..H.VA.FS...TV.PK.N....    45
M3.1        (15-45)    E.H....A..Y.AA.LA...TS.AK.N....    45
H77         (15-45)    E.H....S.G...A.LVG.LTP.AK.N....    45
re43        (15-45)    G.H....S.G.A.A.IAG.LTP.AR.N...V    45
Ge6.3       (15-45)    K.H....S.....S.IA..LTP.AK.NV...    45
C011        (15-45)    K.Y....SQ.QA.F.FT..LQQ.AK.N....    45
TH          (15-45)    E.T....S..HGAL.IA...NQ.AR.N....    45
0115        (15-45)    E.Y....AS..S.FTLVG..KQ.SQ.N...V    45
re4a        (15-45)    Q.Y.S..SSG...S.LV.I.SP.A..NL...    45
q1          (15-45)    E.Y.S..A..Q..ARFAGF.QS.AK.N....    45
q3          (15-45)    E.Y.S..S..Q..A.FVR..ET.PK.N....    45
gh1.tc      (15-45)    S.Y.S..AQ..AAQ.IT...SR.S..K...V    45
M4.1        (15-45)    S.Y....TQG.AAS.LT...SA.A..N....    45
nac5.tc     (15-45)    N.Y.S..T.GH.GH.LTA..SP.A..N....    45
hpcgenanti.p3 (15-45)  S.I.S..TV....HSLA...TQ.A..K....    45
hcj4        (15-45)    E.YTS..A.SH..STLA...SP.A..R...V    45
hpchcv.p2   (15-45)    H.LT...H...L.S.FAG..TP.P..R....    45
hcj1        (15-45)    E.I.S..Q....AMS.LV...TP.AK.N....   45
hct18       (15-45)    E.YTS..N.GH.MT.IVRF.AP.PK.NVH..    45
hct27       (15-45)    T.YT...N.....QALT.F.SP.AK.D....    45
hcve1       (15-45)    E.YT...ST....Q.LV...SR.AK.D....    45
ge12        (15-45)    A.YTS..S.....Q.FA...SL.SQ.K...V    45
LG          (15-45)    A.YT...SV....H.FS...SQ.AK.N....    45
jt.p3.x     (15-45)    V.YT...SQ..H.QSVT.F.TQ.PA.R....    45
us4.tc      (15-45)    H.YT...TV..S.Q.LVGFLSP.P..N....    45
jk1         (15-45)    T.Y.SV.H.SQ..RRVA.F.SP.SA.K...V    45
hpcvjk4.p   (15-45)    T.T.S..H.SQI.R.VT.F.SP.SA.K...V    45
hpce2cor.p  (15-45)    K.SL..VTR..AAARLTA..SS.P..R....    45
hpcns34d.p  (15-45)    G.SL...AR..AAS.LAG..SS.P..R....    45
FT0.1       (15-45)    V.Q.SPPQ.GY..SVLTGILSP.AK.N...V    45
Gj6.1       (15-45)    V.Q.S..Q.GY..SVLTGILSP.AK.N...V    45
re7         (15-45)    G.YTV..AS.F..SRLT...AL.P..R...V    45
hcvkf       (16-46)    N.HTV..TEGFA.QRLT...AL.P..K....    46
arg2.tc     (15-45)    S.RTA..AQ.FN.Y.VA.I.SP.P..R...V    45
hcj6        (15-45)    Q.HTV..ST.HNARTLTGM.SL.AR.K....    45
hpchcj5.p   (15-45)    N.RTVA.S..A...R.FT.M.SS.SK.NL...   45
rs1.pep     (15-45)    Q.RTV..QVGHSVR.FT...SA.SA.N....    45
re71        (15-45)    E.HT...AVSGH..NVLT...SS.S..N....   45
re6         (15-45)    V.RT...EV....ANTFA...TT.P..N..I.   45
hcj8.pep    (15-45)    T.YSS.QE.G..VA.FAG..TT.AK.NLY..    45
re40        (15-45)    S.S.V..RQ.SA.FRFT.F.SR.PT.E.K..    45
hpcencr.p   (15-45)    N.YT.A.SM.QSIYRLTDI.ST.P..KL..V    45
re55b       (15-45)    R.ILMA.RQ.EV.QSFPG..SLAP..K.H..    45
aus1.tc     (15-45)    D.YA...SV.SIMA.IARF.SP.AR.D....    45
PC2.1       (15-44)    E.YA..AS.GHDVSSFAR..AP.AR.N...-    44
hct23       (15-45)    E.HR...S...S.A.VA...TP.AR.N....    45
re34        (15-45)    N.RAV.MVQS...YALT...DS.AA.KL..V    45
```

FIG. 2B

```
Hutchinson   Strains:         395         407

H77          384ETHVTGGSAGRTTAGLVGLLTPGAKQNIQLI414   1977
H90          -----------SVL-IASF--R-P--------        1990

HC-J4        Strains:         395         407

HPCJ483      384ETYTSGGAASHTTSTLASLFSPGASQRIQLV414   1983
J48711       A-------V-------RFT----S--------
J48712       A-----AV--------RFT-F--S--------
J48713       A-----AV--------RFT----S--------        1987
J48714       A-----AV--------GFT----S--------
J48715       ------RV-G------GFT----S--------
HPCJ491      A-------V-GR----GFT----S----K---
J49120       --H-T-RV-G------RFT----S----K---
J49121       --H-T-RVVG------GFT----S----K---         1991
J49122       --H-T-RV-GR-----GFT----S----K---
J49126       T-------V-GR----GFT----S----K---
J49127       K---------------RFT-------------

NY           Strains:         395         407

NY1.1        384STRVTGGQQGRAVHGIASLFSLGASQKIQLV414   t0
NY1.2        --------------Q-F----R-----E----
NY1.3        ---------------------------N---
NY2.1        ------------H-A-SLT---R-----N----       6mo
NY2.2        ------------H-A-SLT---R-----N----
NY3.1        N-------R----A-SLT----P----N----
NY3.2        N-------R----A-SLT----P----N----        -8mo
NY3.3        G-------R----A-SLT----P---EN-R--
NY3.4        ----S--------A-SLT---T-----N----
NY3.5        --H-----AL----AY--T-FL-H-P------
NY4.1        --Q-M---------AYSL---L-P--N-----
NY4.2        --Q-M---------AYSL---LGP--------         14mo
NY4.3        --Q-M---------AYSL---L-P--------

RS           Strains:         395         407

RS1.1.       384RTRTVGGQVGHSVRGFTSLFSAGSAQNIQLI414   t0
RS1.2.       Q-------------------------------
RS1.3.       Q-------------------------D-----
RS2.4.       Q------------------L------------        2mo
RS3.1.       Q------------------L------------        6mo
RS4.1.       Q-----M--G---------L------R-----
RS4.2.       Q-H---M--G---------L------------        8mo
RS5.1.       Q-H---M--G---------L-N----------        11mo
```

Amino Acid Position:

| $ | * | ## | ## | # | ± | @ | ± | ## | # | * | *@ | ## | # | # | ## | ## | @ | @ | $# | ## |
|---|---|---|---|---|---|---|---|---|---|---|---|---|---|---|---|---|---|---|---|---|
| 384 | 385 | 386 | 387 | 388 | 389 | 390 | 391 | 392 | 393 | 394 | 395 | 396 | 397 | 398 | 399 | 400 | 401 | 402 | 403 | 404 | 405 | 406 | 407 |

*(header symbols span positions 384–407)*

% Conserved AA Character for Each AA Position:

49  99  58  100  100  100  97  73  77  100  75  90  100  63  89  100  99  93  100  100  87  87  100  100

Legend

- #$  99–100% identical amino acids (invariantly conserved)
- ##  100% conserved amino acid substitutions (invariantly conserved)
- #   90–99% conserved amino acid substitutions
- @   80–89% conserved amino acid substitutions
- ±   70–79% conserved amino acid substitutions
- *   49–69% conserved amino acid substitutions (highly variable)
- *@  position with the least conserved amino acid substitutions in temporarily sequential time points in individual patients (Figure 3).

Notes:

Positions 403 (F,L), 406 (G,A) and 407 (A,P,S) utilize only 2 or 3 amino acids of homologous character, respectively.

Position 394 represents the only strongly conserved basic amino acid, all others conserved for hydrophobic character and/or size in the case of amino acid position 407.

Position 398 appears to be least conserved between AA 395–407 in sequentially temporal HCV isolates in individual patients (see Fig. 3).

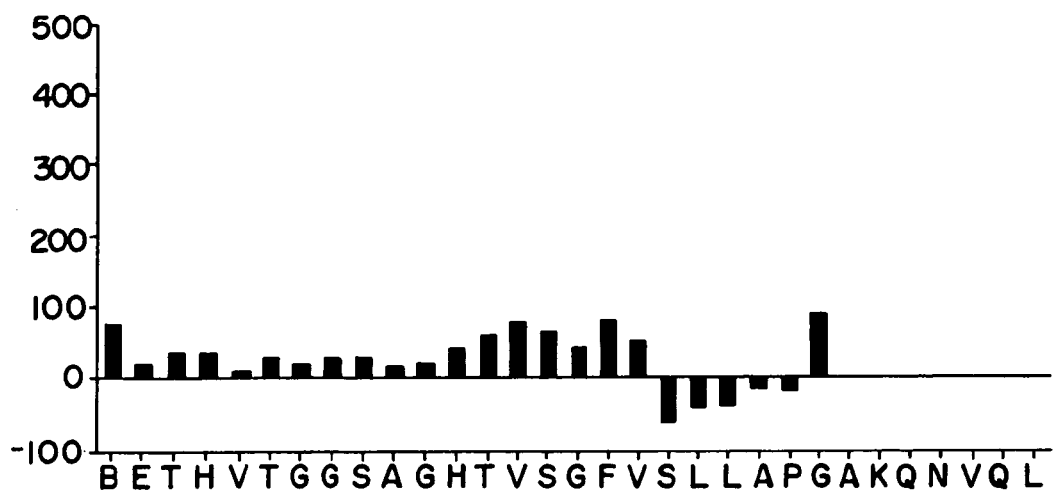
FIG.7A
FIG.7B
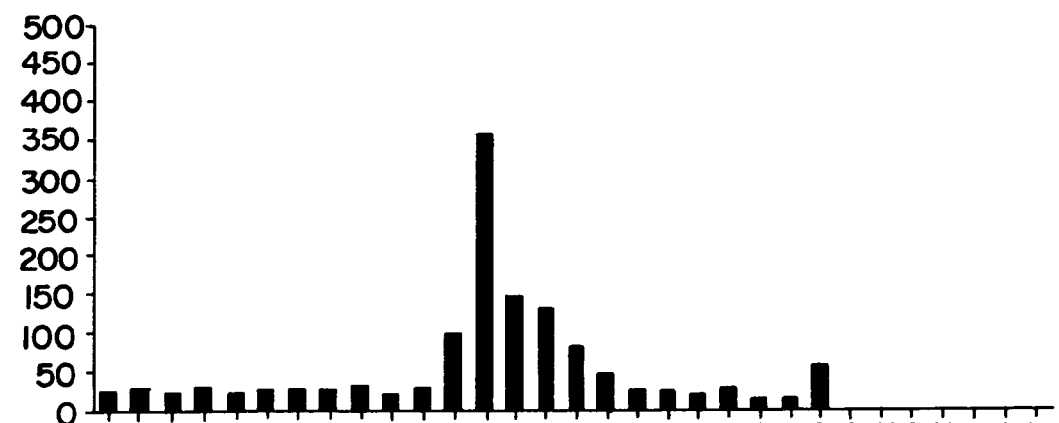
FIG.7C

US 7,098,303 B1

SEQUENCE LISTING

<160> NUMBER OF SEQ ID NOS: 134

<210> SEQ ID NO 1
<211> LENGTH: 6
<212> TYPE: PRT
<213> ORGANISM: Hepatitis C virus
<220> FEATURE:
<221> NAME/KEY: misc_feature
<222> LOCATION: (1)..(1)
<223> OTHER INFORMATION: Represents Ala, Arg, Asp, Gly, Lys, Ser, or Thr
<220> FEATURE:
<221> NAME/KEY: misc_feature

```
<222> LOCATION: (2)..(2)
<223> OTHER INFORMATION: Represents Ile, Leu, Met, Phe or Trp
<220> FEATURE:
<221> NAME/KEY: misc_feature
<222> LOCATION: (3)..(3)
<223> OTHER INFORMATION: Represents Leu or Phe
<220> FEATURE:
<221> NAME/KEY: misc_feature
<222> LOCATION: (4)..(5)
<223> OTHER INFORMATION: Represents any amino acid
<220> FEATURE:
<221> NAME/KEY: misc_feature
<222> LOCATION: (6)..(6)
<223> OTHER INFORMATION: Represents Ala or Gly

<400> SEQUENCE: 1

Xaa Xaa Xaa Xaa Xaa Xaa
1               5

<210> SEQ ID NO 2
<211> LENGTH: 32
<212> TYPE: PRT
<213> ORGANISM: Hepatitis C virus
<220> FEATURE:
<221> NAME/KEY: misc_feature
<222> LOCATION: (1)..(1)
<223> OTHER INFORMATION: acetyl cysteine
<220> FEATURE:
<221> NAME/KEY: misc_feature
<222> LOCATION: (2)..(2)
<223> OTHER INFORMATION: 2-amino heptanoic is butyl alanine

<400> SEQUENCE: 2

Xaa Xaa Glu Thr His Val Thr Gly Gly Ser Ala Gly His Thr Val Ser
1               5                   10                  15

Gly Phe Val Ser Leu Leu Ala Pro Gly Ala Lys Gln Asn Val Gln Leu
            20                  25                  30

<210> SEQ ID NO 3
<211> LENGTH: 5
<212> TYPE: PRT
<213> ORGANISM: Hepatitis C virus

<400> SEQUENCE: 3

Val Ser Leu Leu Ala
1               5

<210> SEQ ID NO 4
<211> LENGTH: 7
<212> TYPE: PRT
<213> ORGANISM: Hepatitis C virus

<400> SEQUENCE: 4

Ser Leu Leu Ala Pro Gly Ala
1               5

<210> SEQ ID NO 5
<211> LENGTH: 5
<212> TYPE: PRT
<213> ORGANISM: Hepatitis C virus

<400> SEQUENCE: 5

Leu Ala Pro Gly Ala
1               5

<210> SEQ ID NO 6
<211> LENGTH: 7
<212> TYPE: PRT
```

-continued

<213> ORGANISM: Hepatitis C virus
<220> FEATURE:
<221> NAME/KEY: misc_feature
<222> LOCATION: (7)..(7)
<223> OTHER INFORMATION: Represents Ala, Pro or Ser
<220> FEATURE:
<221> NAME/KEY: misc_feature
<222> LOCATION: (4)..(5)
<223> OTHER INFORMATION: Represents Any Amino Acid

<400> SEQUENCE: 6

Ser Leu Leu Xaa Xaa Gly Xaa
1 5

<210> SEQ ID NO 7
<211> LENGTH: 7
<212> TYPE: PRT
<213> ORGANISM: Hepatitis C virus
<220> FEATURE:
<221> NAME/KEY: misc_feature
<222> LOCATION: (7)..(7)
<223> OTHER INFORMATION: Represents Ala, Pro or Ser
<220> FEATURE:
<221> NAME/KEY: misc_feature
<222> LOCATION: (4)..(5)
<223> OTHER INFORMATION: Represents Any Amino Acid

<400> SEQUENCE: 7

Ser Leu Phe Xaa Xaa Gly Xaa
1 5

<210> SEQ ID NO 8
<211> LENGTH: 31
<212> TYPE: PRT
<213> ORGANISM: Hepatitis C virus
<220> FEATURE:
<221> NAME/KEY: misc_feature
<222> LOCATION: (1)..(1)
<223> OTHER INFORMATION: Represents Any Amino Acid
<220> FEATURE:
<221> NAME/KEY: misc_feature
<222> LOCATION: (3)..(3)
<223> OTHER INFORMATION: “Represents Any Amino Acid
<220> FEATURE:
<221> NAME/KEY: misc_feature
<222> LOCATION: (8)..(8)
<223> OTHER INFORMATION: ”Represents Any Amino Acid
<220> FEATURE:
<221> NAME/KEY: misc_feature
<222> LOCATION: (14)..(14)
<223> OTHER INFORMATION: “Represents Any Amino Acid
<220> FEATURE:
<221> NAME/KEY: misc_feature
<222> LOCATION: (16)..(16)
<223> OTHER INFORMATION: ”Represents Any Amino Acid
<220> FEATURE:
<221> NAME/KEY: misc_feature
<222> LOCATION: (17)..(17)
<223> OTHER INFORMATION: “Represents Any Amino Acid
<220> FEATURE:
<221> NAME/KEY: misc_feature
<222> LOCATION: (21)..(21)
<223> OTHER INFORMATION: ”Represents Any Amino Acid
<220> FEATURE:
<221> NAME/KEY: misc_feature
<222> LOCATION: (22)..(22)
<223> OTHER INFORMATION: “Represents Any Amino Acid
<220> FEATURE:
<221> NAME/KEY: misc_feature
<222> LOCATION: (24)..(24)
<223> OTHER INFORMATION: ”Represents Any Amino Acid
<220> FEATURE:
<221> NAME/KEY: misc_feature
<222> LOCATION: (27)..(27)
<223> OTHER INFORMATION: “Represents Any Amino Acid -continued

<400> SEQUENCE: 8

Xaa Thr Xaa Val Thr Gly Gly Xaa Ala Ala Arg Thr Thr Xaa Gly Xaa
1 5 10 15

Xaa Ser Leu Phe Xaa Xaa Gly Xaa Ser Gln Xaa Ile Gln Leu Ile
20 25 30

<210> SEQ ID NO 9
<211> LENGTH: 31
<212> TYPE: PRT
<213> ORGANISM: Hepatitis C virus

<400> SEQUENCE: 9

Ala Thr Tyr Ala Thr Gly Ala Ala Gln Gly His Ala Thr Asn Ser Phe
1 5 10 15

Val Ser Leu Phe Arg Ser Gly Ala Ser Gln Asn Leu Lys Leu Val
20 25 30

<210> SEQ ID NO 10
<211> LENGTH: 31
<212> TYPE: PRT
<213> ORGANISM: Hepatitis C virus

<400> SEQUENCE: 10

Ser Thr Gln Val Thr Gly Gly Gln Ala Ala His Thr Val Arg Gly Val
1 5 10 15

Ala Ser Ile Phe Ser Pro Gly Ser Arg Gln Asp Ile Ser Leu Ile
20 25 30

<210> SEQ ID NO 11
<211> LENGTH: 31
<212> TYPE: PRT
<213> ORGANISM: Hepatitis C virus

<400> SEQUENCE: 11

Ser Thr Arg Val Thr Gly Gly Gln Gln Gly Arg Ala Val His Gly Ile
1 5 10 15

Ala Ser Leu Phe Ser Leu Gly Ala Ser Gln Lys Ile Gln Leu Val
20 25 30

<210> SEQ ID NO 12
<211> LENGTH: 31
<212> TYPE: PRT
<213> ORGANISM: Hepatitis C virus

<400> SEQUENCE: 12

Ser Thr His Val Met Gly Ala Gln Gln Gly Arg Val Ala Lys Gly Phe
1 5 10 15

Thr Ser Leu Phe Gly Pro Gly Pro Ala Gln Lys Ile Gly Leu Ile
20 25 30

<210> SEQ ID NO 13
<211> LENGTH: 31
<212> TYPE: PRT
<213> ORGANISM: Hepatitis C virus

<400> SEQUENCE: 13

Ser Thr His Val Thr Gly Ala Val Gln Gly His Ser Ile Arg Gly Leu
1 5 10 15

Thr Ser Leu Phe Thr Ser Gly Pro Ala Gln Lys Ile Gln Leu Val
20 25 30

```
<210> SEQ ID NO 14
<211> LENGTH: 31
<212> TYPE: PRT
<213> ORGANISM: Hepatitis C virus

<400> SEQUENCE: 14

Glu Thr His Val Thr Gly Gly Ile Ala Ala Lys Thr Thr Ala Ser Leu
1               5                   10                  15

Thr Gly Leu Phe Asn Leu Gly Ala Lys Gln Asn Ile Gln Leu Ile
            20                  25                  30

<210> SEQ ID NO 15
<211> LENGTH: 31
<212> TYPE: PRT
<213> ORGANISM: Hepatitis C virus

<400> SEQUENCE: 15

Glu Thr His Val Thr Gly Gly Asn Ala Gly Arg Ala Ala Gly Ile
1               5                   10                  15

Ala Gly Leu Phe Thr Leu Gly Ala Lys Gln Asn Val Gln Leu Ile
            20                  25                  30

<210> SEQ ID NO 16
<211> LENGTH: 31
<212> TYPE: PRT
<213> ORGANISM: Hepatitis C virus

<400> SEQUENCE: 16

Gln Thr Arg Val Thr Gly Gly Thr Ala Ala Gln Ser Thr Ala Arg Ile
1               5                   10                  15

Ala Gly Leu Phe Ser Leu Gly Ala Arg Gln Asn Ile Gln Leu Ile
            20                  25                  30

<210> SEQ ID NO 17
<211> LENGTH: 31
<212> TYPE: PRT
<213> ORGANISM: Hepatitis C virus

<400> SEQUENCE: 17

Gln Thr His Val Met Gly Gly Thr Ala Gly Arg Asn Ala Tyr Gly Leu
1               5                   10                  15

Thr Ser Phe Leu Ser Val Gly Ala Ser Gln Lys Ile Gln Leu Ile
            20                  25                  30

<210> SEQ ID NO 18
<211> LENGTH: 31
<212> TYPE: PRT
<213> ORGANISM: Hepatitis C virus

<400> SEQUENCE: 18

Glu Thr His Val Met Gly Gly Ala Ala Ser Ser Thr Thr Tyr Arg Phe
1               5                   10                  15

Ala Ser Leu Phe Thr Ser Gly Pro Ala Gln Lys Ile Gln Leu Val
            20                  25                  30

<210> SEQ ID NO 19
<211> LENGTH: 31
<212> TYPE: PRT
<213> ORGANISM: Hepatitis C virus

<400> SEQUENCE: 19

Glu Thr His Val Thr Gly Gly Ser Ala Ala Ser Thr Thr Ala Thr Phe
```

-continued

```
                1               5                  10                 15
Ser Lys Leu Phe Met Pro Gly Ala Ser Gln Asn Ile Gln Leu Ile
            20                  25                 30
```

<210> SEQ ID NO 20
<211> LENGTH: 31
<212> TYPE: PRT
<213> ORGANISM: Hepatitis C virus

<400> SEQUENCE: 20

```
Gly Thr Thr Arg Val Gly Gly Ala Ala Ala Arg Thr Thr Ser Ser Phe
1               5                  10                 15
Ala Ser Leu Leu Thr His Gly Pro Ser Gln Asn Ile Gln Leu Val
            20                  25                 30
```

<210> SEQ ID NO 21
<211> LENGTH: 31
<212> TYPE: PRT
<213> ORGANISM: Hepatitis C virus

<400> SEQUENCE: 21

```
Gly Thr His Val Thr Gly Gly Ala Ala Ala Arg Asp Ala Phe Arg Phe
1               5                  10                 15
Ser Ser Leu Phe Thr Arg Gly Pro Ser Gln Asn Ile Gln Leu Ile
            20                  25                 30
```

<210> SEQ ID NO 22
<211> LENGTH: 31
<212> TYPE: PRT
<213> ORGANISM: Hepatitis C virus

<400> SEQUENCE: 22

```
Ala Thr Asn Met Thr Gly Gly Ala Pro Ala Arg Thr Thr Tyr Lys Leu
1               5                  10                 15
Thr Thr Leu Phe Ser Tyr Gly Ala Ser Gln Lys Ile Gln Leu Ile
            20                  25                 30
```

<210> SEQ ID NO 23
<211> LENGTH: 31
<212> TYPE: PRT
<213> ORGANISM: Hepatitis C virus

<400> SEQUENCE: 23

```
His Asn His Val Thr Gly Gly Thr Ser Ala Arg Asn Thr Phe Gly Ile
1               5                  10                 15
Thr Thr Leu Phe Thr Gln Gly Pro Ser Gln Lys Leu Gln Leu Val
            20                  25                 30
```

<210> SEQ ID NO 24
<211> LENGTH: 31
<212> TYPE: PRT
<213> ORGANISM: Hepatitis C virus

<400> SEQUENCE: 24

```
Gly Thr His Val Thr Gly Gly Ala Ala Ala Arg Asn Ala His Ser Leu
1               5                  10                 15
Thr Ser Leu Leu Ala Pro Gly Ala Ser Gln Lys Ile Gln Leu Ile
            20                  25                 30
```

<210> SEQ ID NO 25
<211> LENGTH: 31
<212> TYPE: PRT

<213> ORGANISM: Hepatitis C virus

<400> SEQUENCE: 25

Thr Thr Arg Val Ser Gly Gly Thr Ala Ala His Thr Thr Ala Gly Leu
1               5                   10                  15

Thr Ser Leu Phe Ser Pro Gly Pro Arg Gln Asn Ile His Leu Val
            20                  25                  30

<210> SEQ ID NO 26
<211> LENGTH: 31
<212> TYPE: PRT
<213> ORGANISM: Hepatitis C virus

<400> SEQUENCE: 26

Thr Thr His Val Ser Gly Gly Thr Ala Gly Arg Thr Thr Ala Ser Leu
1               5                   10                  15

Thr Ser Phe Phe Ala Pro Gly Ala Ser Gln Arg Ile Gln Leu Val
            20                  25                  30

<210> SEQ ID NO 27
<211> LENGTH: 31
<212> TYPE: PRT
<213> ORGANISM: Hepatitis C virus

<400> SEQUENCE: 27

Thr Thr His Val Thr Gly Gly Ala Thr Gly His Thr Thr Ser Gly Ile
1               5                   10                  15

Ala Ser Leu Phe Leu Pro Gly Ala Ser Gln Lys Ile Gln Leu Ile
            20                  25                  30

<210> SEQ ID NO 28
<211> LENGTH: 31
<212> TYPE: PRT
<213> ORGANISM: Hepatitis C virus

<400> SEQUENCE: 28

Asp Thr Tyr Ala Ser Gly Gly Ala Gln Gly Arg Ser Thr Leu Gly Phe
1               5                   10                  15

Thr Ser Leu Phe Thr Pro Gly Ala Ser Gln Lys Ile Gln Leu Ile
            20                  25                  30

<210> SEQ ID NO 29
<211> LENGTH: 31
<212> TYPE: PRT
<213> ORGANISM: Hepatitis C virus

<400> SEQUENCE: 29

Asp Thr Tyr Ala Ser Gly Gly Ala Ala Gly Arg Ala Thr Tyr Gly Ile
1               5                   10                  15

Thr Ser Leu Phe Ala Pro Gly Ala Ser Gln Asn Ile Gln Leu Ile
            20                  25                  30

<210> SEQ ID NO 30
<211> LENGTH: 31
<212> TYPE: PRT
<213> ORGANISM: Hepatitis C virus

<400> SEQUENCE: 30

Arg Thr Tyr Ala Ser Gly Gly Ala Ala Gly Arg Thr Thr His Gly Phe
1               5                   10                  15

Thr Ser Leu Phe Ser Thr Gly Ala Arg Gln Asn Ile Gln Leu Ile
            20                  25                  30

-continued

<210> SEQ ID NO 31
<211> LENGTH: 31
<212> TYPE: PRT
<213> ORGANISM: Hepatitis C virus

<400> SEQUENCE: 31

Gln Thr Tyr Val Thr Gly Gly Lys Ala Ala Gln Thr Val Ser Gly Phe
1               5                   10                  15

Thr Gly Leu Phe Ser Ser Gly Pro Ser Gln Lys Ile Gln Leu Ile
            20                  25                  30

<210> SEQ ID NO 32
<211> LENGTH: 31
<212> TYPE: PRT
<213> ORGANISM: Hepatitis C virus

<400> SEQUENCE: 32

Asp Thr Tyr Val Ser Gly Gly Ala Ala Ala Arg Ser Ile Ser Gly Phe
1               5                   10                  15

Thr Ser Leu Phe Thr Pro Gly Ala Ser Gln Lys Ile Gln Leu Val
            20                  25                  30

<210> SEQ ID NO 33
<211> LENGTH: 31
<212> TYPE: PRT
<213> ORGANISM: Hepatitis C virus

<400> SEQUENCE: 33

Ser Thr Tyr Val Thr Gly Gly Glu Ala Ser Arg Thr Thr Arg Gly Phe
1               5                   10                  15

Ala Ser Leu Phe Thr Leu Gly Ser Ser Gln Lys Ile Gln Leu Ile
            20                  25                  30

<210> SEQ ID NO 34
<211> LENGTH: 31
<212> TYPE: PRT
<213> ORGANISM: Hepatitis C virus

<400> SEQUENCE: 34

Asn Thr Tyr Val Thr Gly Gly Ser Ala Gly Arg Ala Val Ala Gly Phe
1               5                   10                  15

Ala Gly Leu Leu Gln Pro Gly Ala Lys Gln Asn Val Gln Leu Ile
            20                  25                  30

<210> SEQ ID NO 35
<211> LENGTH: 31
<212> TYPE: PRT
<213> ORGANISM: Hepatitis C virus

<400> SEQUENCE: 35

His Thr Arg Val Thr Gly Gly Gln Val Ala Phe Arg Thr His Gly Leu
1               5                   10                  15

Val Ser Leu Phe Thr Gln Gly Pro Ser Gln Lys Ile Gln Leu Val
            20                  25                  30

<210> SEQ ID NO 36
<211> LENGTH: 31
<212> TYPE: PRT
<213> ORGANISM: Hepatitis C virus

<400> SEQUENCE: 36

-continued

His Thr His Val Thr Gly Gly Arg Val Ala Ser Ser Thr Gln Ser Leu
1               5                   10                  15

Val Ser Trp Leu Ser Gln Gly Pro Ser Gln Lys Ile Gln Leu Val
            20                  25                  30

<210> SEQ ID NO 37
<211> LENGTH: 31
<212> TYPE: PRT
<213> ORGANISM: Hepatitis C virus

<400> SEQUENCE: 37

His Thr Arg Val Thr Gly Gly Val Gln Gly His Val Thr Ser Thr Leu
1               5                   10                  15

Thr Ser Leu Phe Arg Pro Gly Ala Ser Gln Lys Ile Gln Leu Val
            20                  25                  30

<210> SEQ ID NO 38
<211> LENGTH: 31
<212> TYPE: PRT
<213> ORGANISM: Hepatitis C virus

<400> SEQUENCE: 38

Asn Thr Arg Val Thr Gly Gly Val Gln Gly Arg Asp Thr Ser Gly Leu
1               5                   10                  15

Val Ser Leu Phe Ser Leu Gly Pro Ser Gln Lys Ile Gln Leu Val
            20                  25                  30

<210> SEQ ID NO 39
<211> LENGTH: 31
<212> TYPE: PRT
<213> ORGANISM: Hepatitis C virus

<400> SEQUENCE: 39

Asp Thr His Val Thr Gly Gly Ala Gln Ala Lys Thr Thr Asn Arg Leu
1               5                   10                  15

Val Ser Met Phe Ala Ser Gly Pro Ser Gln Lys Ile Gln Leu Ile
            20                  25                  30

<210> SEQ ID NO 40
<211> LENGTH: 31
<212> TYPE: PRT
<213> ORGANISM: Hepatitis C virus

<400> SEQUENCE: 40

Glu Thr His Val Thr Gly Gly Ala Ser Ala Arg Thr Thr Gln Arg Phe
1               5                   10                  15

Thr Ser Phe Phe Asp Leu Gly Pro Ser Gln Lys Ile Gln Leu Val
            20                  25                  30

<210> SEQ ID NO 41
<211> LENGTH: 31
<212> TYPE: PRT
<213> ORGANISM: Hepatitis C virus

<400> SEQUENCE: 41

Thr Thr Tyr Met Thr Gly Gly Ala Asn Ala Arg Thr Thr Gln Gly Phe
1               5                   10                  15

Val Ser Leu Phe Thr Pro Gly Pro Ala Gln Lys Ile Gln Leu Val
            20                  25                  30

<210> SEQ ID NO 42
<211> LENGTH: 31

```
<212> TYPE: PRT
<213> ORGANISM: Hepatitis C virus

<400> SEQUENCE: 42

Glu Thr His Val Thr Gly Gly Thr Ser Ala Arg Thr Thr Gln Gly Phe
1               5                   10                  15

Val Ser Leu Phe Ser Ala Gly Ala Ser Gln Lys Ile Gln Leu Val
            20                  25                  30

<210> SEQ ID NO 43
<211> LENGTH: 31
<212> TYPE: PRT
<213> ORGANISM: Hepatitis C virus

<400> SEQUENCE: 43

Gly Thr His Val Thr Gly Gly Gln Ala Ala Arg Thr Thr Gln Ser Phe
1               5                   10                  15

Thr Ser Leu Phe Ser Pro Gly Pro Gln Gln Lys Ile Gln Leu Ile
            20                  25                  30

<210> SEQ ID NO 44
<211> LENGTH: 31
<212> TYPE: PRT
<213> ORGANISM: Hepatitis C virus

<400> SEQUENCE: 44

Arg Thr His Val Thr Gly Gly Lys Ala Ala His Thr Thr Lys Gly Phe
1               5                   10                  15

Ala Ser Leu Phe Thr Pro Gly Pro Ser Gln Asn Ile Gln Leu Ile
            20                  25                  30

<210> SEQ ID NO 45
<211> LENGTH: 31
<212> TYPE: PRT
<213> ORGANISM: Hepatitis C virus

<400> SEQUENCE: 45

Glu Thr Arg Val Thr Gly Ala Val Gln Gly His Gly Ala Leu Gly Leu
1               5                   10                  15

Ala Ser Leu Phe Thr Pro Gly Pro Ser Gln Lys Ile Gln Leu Ile
            20                  25                  30

<210> SEQ ID NO 46
<211> LENGTH: 31
<212> TYPE: PRT
<213> ORGANISM: Hepatitis C virus

<400> SEQUENCE: 46

Glu Thr Arg Val Thr Gly Ala Ile Ala Gly Arg Thr Ala Ser Ser Phe
1               5                   10                  15

Ala Gly Leu Phe Thr Ser Gly Ala Ser Gln Lys Ile Gln Leu Val
            20                  25                  30

<210> SEQ ID NO 47
<211> LENGTH: 31
<212> TYPE: PRT
<213> ORGANISM: Hepatitis C virus

<400> SEQUENCE: 47

Glu Thr Arg Val Thr Gly Gln Gln Val Gly Arg Thr Thr Gln Ser Leu
1               5                   10                  15

Thr Ser Leu Phe Thr Pro Gly Pro Ser Gln Thr Ile Gln Leu Ile
```

-continued 20         25         30

<210> SEQ ID NO 48
<211> LENGTH: 31
<212> TYPE: PRT
<213> ORGANISM: Hepatitis C virus

<400> SEQUENCE: 48

Gln Thr Arg Val Thr Gly Ala Gln Val Gly Arg Thr Thr Ser Ser Leu
1       5         10         15

Thr Ser Leu Phe Thr Pro Gly Pro Ser Gln Asn Ile Gln Leu Val
      20         25         30

<210> SEQ ID NO 49
<211> LENGTH: 31
<212> TYPE: PRT
<213> ORGANISM: Hepatitis C virus

<400> SEQUENCE: 49

Arg Thr Gln Val Thr Gly Ala Gln Ala Gly His Thr Thr Ser Gly Leu
1       5         10         15

Ala Ser Leu Phe Thr Pro Gly Pro Ser Gln Lys Ile Gln Leu Val
      20         25         30

<210> SEQ ID NO 50
<211> LENGTH: 31
<212> TYPE: PRT
<213> ORGANISM: Hepatitis C virus

<400> SEQUENCE: 50

Glu Thr His Val Thr Gly Gly Ser Ala Gly His Thr Val Ser Gly Phe
1       5         10         15

Val Ser Leu Leu Ala Pro Gly Ala Lys Gln Asn Val Gln Leu Ile
      20         25         30

<210> SEQ ID NO 51
<211> LENGTH: 31
<212> TYPE: PRT
<213> ORGANISM: Hepatitis C virus

<400> SEQUENCE: 51

Glu Thr His Val Thr Gly Gly Ser Ala Gly His Thr Val Thr Gly Ile
1       5         10         15

Ala Ser Leu Phe Thr Ser Gly Ala Lys Gln Asn Ile Gln Leu Ile
      20         25         30

<210> SEQ ID NO 52
<211> LENGTH: 31
<212> TYPE: PRT
<213> ORGANISM: Hepatitis C virus

<400> SEQUENCE: 52

Ser Thr His Val Thr Gly Gly Thr Ala Ala His Thr Val Ala Gly Phe
1       5         10         15

Ser Ser Leu Phe Thr Val Gly Pro Lys Gln Asn Ile Gln Leu Ile
      20         25         30

<210> SEQ ID NO 53
<211> LENGTH: 31
<212> TYPE: PRT
<213> ORGANISM: Hepatitis C virus

<400> SEQUENCE: 53

```
Glu Thr His Val Thr Gly Gly Ala Ala Ala Tyr Thr Ala Ala Gly Leu
1               5                   10                  15

Ala Ser Leu Phe Thr Ser Gly Ala Lys Gln Asn Ile Gln Leu Ile
            20                  25                  30
```

<210> SEQ ID NO 54
<211> LENGTH: 31
<212> TYPE: PRT
<213> ORGANISM: Hepatitis C virus

<400> SEQUENCE: 54

```
Glu Thr His Val Thr Gly Gly Ser Ala Gly Arg Thr Thr Ala Gly Leu
1               5                   10                  15

Val Gly Leu Leu Thr Pro Gly Ala Lys Gln Asn Ile Gln Leu Ile
            20                  25                  30
```

<210> SEQ ID NO 55
<211> LENGTH: 31
<212> TYPE: PRT
<213> ORGANISM: Hepatitis C virus

<400> SEQUENCE: 55

```
Gly Thr His Val Thr Gly Gly Ser Ala Gly Arg Ala Thr Ala Gly Ile
1               5                   10                  15

Ala Gly Leu Leu Thr Pro Gly Ala Arg Gln Asn Ile Gln Leu Val
            20                  25                  30
```

<210> SEQ ID NO 56
<211> LENGTH: 31
<212> TYPE: PRT
<213> ORGANISM: Hepatitis C virus

<400> SEQUENCE: 56

```
Lys Thr His Val Thr Gly Gly Ser Ala Ala Arg Thr Thr Ser Gly Ile
1               5                   10                  15

Ala Ser Leu Leu Thr Pro Gly Ala Lys Gln Asn Val Gln Leu Ile
            20                  25                  30
```

<210> SEQ ID NO 57
<211> LENGTH: 31
<212> TYPE: PRT
<213> ORGANISM: Hepatitis C virus

<400> SEQUENCE: 57

```
Lys Thr Tyr Val Thr Gly Gly Ser Gln Ala Gln Ala Thr Phe Gly Phe
1               5                   10                  15

Thr Ser Leu Leu Gln Gln Gly Ala Lys Gln Asn Ile Gln Leu Ile
            20                  25                  30
```

<210> SEQ ID NO 58
<211> LENGTH: 31
<212> TYPE: PRT
<213> ORGANISM: Hepatitis C virus

<400> SEQUENCE: 58

```
Glu Thr Thr Val Thr Gly Gly Ser Ala Ala His Gly Ala Leu Gly Ile
1               5                   10                  15

Ala Ser Leu Phe Asn Gln Gly Ala Arg Gln Asn Ile Gln Leu Ile
            20                  25                  30
```

<210> SEQ ID NO 59

```
<211> LENGTH: 31
<212> TYPE: PRT
<213> ORGANISM: Hepatitis C virus

<400> SEQUENCE: 59

Glu Thr Tyr Val Thr Gly Gly Ala Ser Ala Arg Ser Thr Phe Thr Leu
1               5                   10                  15

Val Gly Leu Phe Lys Gln Gly Ser Gln Gln Asn Ile Gln Leu Val
            20                  25                  30

<210> SEQ ID NO 60
<211> LENGTH: 31
<212> TYPE: PRT
<213> ORGANISM: Hepatitis C virus

<400> SEQUENCE: 60

Gln Thr Tyr Val Ser Gly Gly Ser Gly Arg Thr Thr Ser Gly Leu
1               5                   10                  15

Val Ser Ile Phe Ser Pro Gly Ala Ser Gln Asn Leu Gln Leu Ile
            20                  25                  30

<210> SEQ ID NO 61
<211> LENGTH: 31
<212> TYPE: PRT
<213> ORGANISM: Hepatitis C virus

<400> SEQUENCE: 61

Glu Thr Tyr Val Ser Gly Gly Ala Ala Ala Gln Thr Thr Ala Arg Phe
1               5                   10                  15

Ala Gly Phe Phe Gln Ser Gly Ala Lys Gln Asn Ile Gln Leu Ile
            20                  25                  30

<210> SEQ ID NO 62
<211> LENGTH: 31
<212> TYPE: PRT
<213> ORGANISM: Hepatitis C virus

<400> SEQUENCE: 62

Glu Thr Tyr Val Ser Gly Gly Ser Ala Ala Gln Thr Thr Ala Gly Phe
1               5                   10                  15

Val Arg Leu Phe Glu Thr Gly Pro Lys Gln Asn Ile Gln Leu Ile
            20                  25                  30

<210> SEQ ID NO 63
<211> LENGTH: 31
<212> TYPE: PRT
<213> ORGANISM: Hepatitis C virus

<400> SEQUENCE: 63

Ser Thr Tyr Val Ser Gly Gly Ala Gln Ala Arg Ala Ala Gln Gly Ile
1               5                   10                  15

Thr Ser Leu Phe Ser Arg Gly Ser Gln Lys Ile Gln Leu Val
            20                  25                  30

<210> SEQ ID NO 64
<211> LENGTH: 31
<212> TYPE: PRT
<213> ORGANISM: Hepatitis C virus

<400> SEQUENCE: 64

Ser Thr Tyr Val Thr Gly Gly Thr Gln Gly Arg Ala Ala Ser Gly Leu
1               5                   10                  15
```

```
Thr Ser Leu Phe Ser Ala Gly Ala Ser Gln Asn Ile Gln Leu Ile
            20                  25                  30

<210> SEQ ID NO 65
<211> LENGTH: 31
<212> TYPE: PRT
<213> ORGANISM: Hepatitis C virus

<400> SEQUENCE: 65

Asn Thr Tyr Val Ser Gly Gly Thr Ala Gly His Thr Gly His Gly Leu
 1               5                  10                  15

Thr Ala Leu Phe Ser Pro Gly Ala Ser Gln Asn Ile Gln Leu Ile
            20                  25                  30

<210> SEQ ID NO 66
<211> LENGTH: 31
<212> TYPE: PRT
<213> ORGANISM: Hepatitis C virus

<400> SEQUENCE: 66

Ser Thr Ile Val Ser Gly Gly Thr Val Ala Arg Thr Thr His Ser Leu
 1               5                  10                  15

Ala Ser Leu Phe Thr Gln Gly Ala Ser Gln Lys Ile Gln Leu Ile
            20                  25                  30

<210> SEQ ID NO 67
<211> LENGTH: 31
<212> TYPE: PRT
<213> ORGANISM: Hepatitis C virus

<400> SEQUENCE: 67

Glu Thr Tyr Thr Ser Gly Gly Ala Ala Ser His Thr Thr Ser Thr Leu
 1               5                  10                  15

Ala Ser Leu Phe Ser Pro Gly Ala Ser Gln Arg Ile Gln Leu Val
            20                  25                  30

<210> SEQ ID NO 68
<211> LENGTH: 31
<212> TYPE: PRT
<213> ORGANISM: Hepatitis C virus

<400> SEQUENCE: 68

His Thr Leu Thr Thr Gly Gly His Ala Ala Arg Leu Thr Ser Gly Phe
 1               5                  10                  15

Ala Gly Leu Phe Thr Pro Gly Pro Ser Gln Arg Ile Gln Leu Ile
            20                  25                  30

<210> SEQ ID NO 69
<211> LENGTH: 31
<212> TYPE: PRT
<213> ORGANISM: Hepatitis C virus

<400> SEQUENCE: 69

Glu Thr Ile Val Ser Gly Gly Gln Ala Ala Arg Ala Met Ser Gly Leu
 1               5                  10                  15

Val Ser Leu Phe Thr Pro Gly Ala Lys Gln Asn Ile Gln Leu Ile
            20                  25                  30

<210> SEQ ID NO 70
<211> LENGTH: 31
<212> TYPE: PRT
<213> ORGANISM: Hepatitis C virus
```

-continued

```
<400> SEQUENCE: 70

Glu Thr Tyr Thr Ser Gly Gly Asn Ala Gly His Thr Met Thr Gly Ile
1               5                   10                  15

Val Arg Phe Phe Ala Pro Gly Pro Lys Gln Asn Val His Leu Ile
            20                  25                  30

<210> SEQ ID NO 71
<211> LENGTH: 31
<212> TYPE: PRT
<213> ORGANISM: Hepatitis C virus

<400> SEQUENCE: 71

Thr Thr Tyr Thr Thr Gly Gly Asn Ala Ala Arg Thr Thr Gln Ala Leu
1               5                   10                  15

Thr Ser Phe Phe Ser Pro Gly Ala Lys Gln Asp Ile Gln Leu Ile
            20                  25                  30

<210> SEQ ID NO 72
<211> LENGTH: 31
<212> TYPE: PRT
<213> ORGANISM: Hepatitis C virus

<400> SEQUENCE: 72

Glu Thr Tyr Thr Thr Gly Gly Ser Thr Ala Arg Thr Thr Gln Gly Leu
1               5                   10                  15

Val Ser Leu Phe Ser Arg Gly Ala Lys Gln Asp Ile Gln Leu Ile
            20                  25                  30

<210> SEQ ID NO 73
<211> LENGTH: 31
<212> TYPE: PRT
<213> ORGANISM: Hepatitis C virus

<400> SEQUENCE: 73

Ala Thr Tyr Thr Ser Gly Gly Ser Ala Ala Arg Thr Thr Gln Gly Phe
1               5                   10                  15

Ala Ser Leu Phe Ser Leu Gly Ser Gln Gln Lys Ile Gln Leu Val
            20                  25                  30

<210> SEQ ID NO 74
<211> LENGTH: 31
<212> TYPE: PRT
<213> ORGANISM: Hepatitis C virus

<400> SEQUENCE: 74

Ala Thr Tyr Thr Thr Gly Gly Ser Val Ala Arg Thr Thr His Gly Phe
1               5                   10                  15

Ser Ser Leu Phe Ser Gln Gly Ala Lys Gln Asn Ile Gln Leu Ile
            20                  25                  30

<210> SEQ ID NO 75
<211> LENGTH: 31
<212> TYPE: PRT
<213> ORGANISM: Hepatitis C virus

<400> SEQUENCE: 75

Val Thr Tyr Thr Thr Gly Gly Ser Gln Ala Arg His Thr Gln Ser Val
1               5                   10                  15

Thr Ser Phe Phe Thr Gln Gly Pro Ala Gln Arg Ile Gln Leu Ile
            20                  25                  30
```

-continued

<210> SEQ ID NO 76
<211> LENGTH: 31
<212> TYPE: PRT
<213> ORGANISM: Hepatitis C virus

<400> SEQUENCE: 76

His Thr Tyr Thr Thr Gly Gly Thr Val Ala Arg Ser Thr Gln Gly Leu
1               5                   10                  15

Val Gly Phe Leu Ser Pro Gly Pro Ser Gln Asn Ile Gln Leu Ile
            20                  25                  30

<210> SEQ ID NO 77
<211> LENGTH: 31
<212> TYPE: PRT
<213> ORGANISM: Hepatitis C virus

<400> SEQUENCE: 77

Thr Thr Tyr Val Ser Val Gly His Ala Ser Gln Thr Thr Arg Arg Val
1               5                   10                  15

Ala Ser Phe Phe Ser Pro Gly Ser Ala Gln Lys Ile Gln Leu Val
            20                  25                  30

<210> SEQ ID NO 78
<211> LENGTH: 31
<212> TYPE: PRT
<213> ORGANISM: Hepatitis C virus

<400> SEQUENCE: 78

Thr Thr Thr Val Ser Gly Gly His Ala Ser Gln Ile Thr Arg Gly Val
1               5                   10                  15

Thr Ser Phe Phe Ser Pro Gly Ser Ala Gln Lys Ile Gln Leu Val
            20                  25                  30

<210> SEQ ID NO 79
<211> LENGTH: 31
<212> TYPE: PRT
<213> ORGANISM: Hepatitis C virus

<400> SEQUENCE: 79

Lys Thr Ser Leu Thr Gly Val Thr Arg Ala Arg Ala Ala Ala Arg Leu
1               5                   10                  15

Thr Ala Leu Phe Ser Ser Gly Pro Ser Gln Arg Ile Gln Leu Ile
            20                  25                  30

<210> SEQ ID NO 80
<211> LENGTH: 31
<212> TYPE: PRT
<213> ORGANISM: Hepatitis C virus

<400> SEQUENCE: 80

Gly Thr Ser Leu Thr Gly Gly Ala Arg Ala Arg Ala Ala Ser Gly Leu
1               5                   10                  15

Ala Gly Leu Phe Ser Ser Gly Pro Ser Gln Arg Ile Gln Leu Ile
            20                  25                  30

<210> SEQ ID NO 81
<211> LENGTH: 31
<212> TYPE: PRT
<213> ORGANISM: Hepatitis C virus

<400> SEQUENCE: 81

Val Thr Gln Val Ser Pro Pro Gln Ala Gly Tyr Thr Thr Ser Val Leu
1               5                   10                  15

```
Thr Gly Ile Leu Ser Pro Gly Ala Lys Gln Asn Ile Gln Leu Val
            20                  25                  30

<210> SEQ ID NO 82
<211> LENGTH: 31
<212> TYPE: PRT
<213> ORGANISM: Hepatitis C virus

<400> SEQUENCE: 82

Val Thr Gln Val Ser Gly Gly Gln Ala Gly Tyr Thr Thr Ser Val Leu
1               5                   10                  15

Thr Gly Ile Leu Ser Pro Gly Ala Lys Gln Asn Ile Gln Leu Val
            20                  25                  30

<210> SEQ ID NO 83
<211> LENGTH: 31
<212> TYPE: PRT
<213> ORGANISM: Hepatitis C virus

<400> SEQUENCE: 83

Gly Thr Tyr Thr Val Gly Gly Ala Ser Ala Phe Thr Thr Ser Arg Leu
1               5                   10                  15

Thr Ser Leu Phe Ala Leu Gly Pro Ser Gln Arg Ile Gln Leu Val
            20                  25                  30

<210> SEQ ID NO 84
<211> LENGTH: 31
<212> TYPE: PRT
<213> ORGANISM: Hepatitis C virus

<400> SEQUENCE: 84

Asn Thr His Thr Val Gly Gly Thr Glu Gly Phe Ala Thr Gln Arg Leu
1               5                   10                  15

Thr Ser Leu Phe Ala Leu Gly Pro Ser Gln Lys Ile Gln Leu Ile
            20                  25                  30

<210> SEQ ID NO 85
<211> LENGTH: 31
<212> TYPE: PRT
<213> ORGANISM: Hepatitis C virus

<400> SEQUENCE: 85

Ser Thr Arg Thr Ala Gly Gly Ala Gln Ala Phe Asn Thr Tyr Gly Val
1               5                   10                  15

Ala Ser Ile Phe Ser Pro Gly Pro Ser Gln Arg Ile Gln Leu Val
            20                  25                  30

<210> SEQ ID NO 86
<211> LENGTH: 31
<212> TYPE: PRT
<213> ORGANISM: Hepatitis C virus

<400> SEQUENCE: 86

Gln Thr His Thr Val Gly Gly Ser Thr Ala His Asn Ala Arg Thr Leu
1               5                   10                  15

Thr Gly Met Phe Ser Leu Gly Ala Arg Gln Lys Ile Gln Leu Ile
            20                  25                  30

<210> SEQ ID NO 87
<211> LENGTH: 31
<212> TYPE: PRT
<213> ORGANISM: Hepatitis C virus
```

-continued

<400> SEQUENCE: 87

Asn Thr Arg Thr Val Ala Gly Ser Ala Ala Thr Arg Gly Phe
1               5                   10                  15

Thr Ser Met Phe Ser Ser Gly Ser Lys Gln Asn Leu Gln Leu Ile
            20                  25                  30

<210> SEQ ID NO 88
<211> LENGTH: 31
<212> TYPE: PRT
<213> ORGANISM: Hepatitis C virus

<400> SEQUENCE: 88

Gln Thr Arg Thr Val Gly Gly Gln Val Gly His Ser Val Arg Gly Phe
1               5                   10                  15

Thr Ser Leu Phe Ser Ala Gly Ser Ala Gln Asn Ile Gln Leu Ile
            20                  25                  30

<210> SEQ ID NO 89
<211> LENGTH: 31
<212> TYPE: PRT
<213> ORGANISM: Hepatitis C virus

<400> SEQUENCE: 89

Glu Thr His Thr Thr Gly Ala Val Ser Gly His Thr Thr Asn Val Leu
1               5                   10                  15

Thr Ser Leu Phe Ser Ser Gly Ser Ser Gln Asn Ile Gln Leu Ile
            20                  25                  30

<210> SEQ ID NO 90
<211> LENGTH: 31
<212> TYPE: PRT
<213> ORGANISM: Hepatitis C virus

<400> SEQUENCE: 90

Val Thr Arg Thr Thr Gly Glu Val Ala Ala Arg Thr Ala Asn Thr Phe
1               5                   10                  15

Ala Ser Leu Phe Thr Thr Gly Pro Ser Gln Asn Ile Gln Leu Ile
            20                  25                  30

<210> SEQ ID NO 91
<211> LENGTH: 31
<212> TYPE: PRT
<213> ORGANISM: Hepatitis C virus

<400> SEQUENCE: 91

Thr Thr Tyr Ser Ser Gly Gln Glu Ala Gly Arg Thr Val Ala Gly Phe
1               5                   10                  15

Ala Gly Leu Phe Thr Thr Gly Ala Lys Gln Asn Leu Tyr Leu Ile
            20                  25                  30

<210> SEQ ID NO 92
<211> LENGTH: 31
<212> TYPE: PRT
<213> ORGANISM: Hepatitis C virus

<400> SEQUENCE: 92

Ser Thr Ser Val Val Gly Gly Arg Gln Ala Ser Ala Thr Phe Arg Phe
1               5                   10                  15

Thr Ser Phe Phe Ser Arg Gly Pro Thr Gln Glu Ile Lys Leu Ile
            20                  25                  30

<210> SEQ ID NO 93
<211> LENGTH: 31
<212> TYPE: PRT
<213> ORGANISM: Hepatitis C virus

<400> SEQUENCE: 93

Asn Thr Tyr Thr Thr Ala Gly Ser Met Ala Gln Ser Ile Tyr Arg Leu
1               5                   10                  15

Thr Asp Ile Phe Ser Thr Gly Pro Ser Gln Lys Leu Gln Leu Val
            20                  25                  30

<210> SEQ ID NO 94
<211> LENGTH: 31
<212> TYPE: PRT
<213> ORGANISM: Hepatitis C virus

<400> SEQUENCE: 94

Arg Thr Ile Leu Met Ala Gly Arg Gln Ala Glu Val Thr Gln Ser Phe
1               5                   10                  15

Pro Gly Leu Phe Ser Leu Ala Pro Ser Gln Lys Ile His Leu Ile
            20                  25                  30

<210> SEQ ID NO 95
<211> LENGTH: 31
<212> TYPE: PRT
<213> ORGANISM: Hepatitis C virus

<400> SEQUENCE: 95

Asp Thr Tyr Ala Thr Gly Gly Ser Val Ala Ser Ile Met Ala Gly Ile
1               5                   10                  15

Ala Arg Phe Phe Ser Pro Gly Ala Arg Gln Asp Ile Gln Leu Ile
            20                  25                  30

<210> SEQ ID NO 96
<211> LENGTH: 30
<212> TYPE: PRT
<213> ORGANISM: Hepatitis C virus

<400> SEQUENCE: 96

Glu Thr Tyr Ala Thr Gly Ala Ser Ala Gly His Asp Val Ser Ser Phe
1               5                   10                  15

Ala Arg Leu Phe Ala Pro Gly Ala Arg Gln Asn Ile Gln Ile
            20                  25                  30

<210> SEQ ID NO 97
<211> LENGTH: 31
<212> TYPE: PRT
<213> ORGANISM: Hepatitis C virus

<400> SEQUENCE: 97

Glu Thr His Arg Thr Gly Gly Ser Ala Ala Arg Ser Thr Ala Gly Val
1               5                   10                  15

Ala Ser Leu Phe Thr Pro Gly Ala Arg Gln Asn Ile Gln Leu Ile
            20                  25                  30

<210> SEQ ID NO 98
<211> LENGTH: 31
<212> TYPE: PRT
<213> ORGANISM: Hepatitis C virus

<400> SEQUENCE: 98

Asn Thr Arg Ala Val Gly Met Val Gln Ser Arg Thr Thr Tyr Ala Leu

```
                1               5                   10                  15
Thr Ser Leu Phe Asp Ser Gly Ala Ala Gln Lys Leu Gln Leu Val
            20                  25                  30

<210> SEQ ID NO 99
<211> LENGTH: 31
<212> TYPE: PRT
<213> ORGANISM: Hepatitis C virus

<400> SEQUENCE: 99

Glu Thr His Val Thr Gly Gly Ser Ala Gly Arg Thr Thr Ala Gly Leu
1               5                   10                  15

Val Gly Leu Leu Thr Pro Gly Ala Lys Gln Asn Ile Gln Leu Ile
            20                  25                  30

<210> SEQ ID NO 100
<211> LENGTH: 31
<212> TYPE: PRT
<213> ORGANISM: Hepatitis C virus

<400> SEQUENCE: 100

Glu Thr His Val Thr Gly Gly Ser Ala Gly Arg Ser Val Leu Gly Ile
1               5                   10                  15

Ala Ser Phe Leu Thr Arg Gly Pro Lys Gln Asn Ile Gln Leu Ile
            20                  25                  30

<210> SEQ ID NO 101
<211> LENGTH: 31
<212> TYPE: PRT
<213> ORGANISM: Hepatitis C virus

<400> SEQUENCE: 101

Glu Thr Tyr Thr Ser Gly Gly Ala Ala Ser His Thr Thr Ser Thr Leu
1               5                   10                  15

Ala Ser Leu Phe Ser Pro Gly Ala Ser Gln Arg Ile Gln Leu Val
            20                  25                  30

<210> SEQ ID NO 102
<211> LENGTH: 31
<212> TYPE: PRT
<213> ORGANISM: Hepatitis C virus

<400> SEQUENCE: 102

Ala Thr Tyr Thr Ser Gly Gly Val Ala Ser His Thr Thr Ser Arg Phe
1               5                   10                  15

Thr Ser Leu Phe Ser Ser Gly Ala Ser Gln Arg Ile Gln Leu Val
            20                  25                  30

<210> SEQ ID NO 103
<211> LENGTH: 31
<212> TYPE: PRT
<213> ORGANISM: Hepatitis C virus

<400> SEQUENCE: 103

Ala Thr Tyr Thr Ser Gly Ala Val Ala Ser His Thr Thr Ser Arg Phe
1               5                   10                  15

Thr Ser Phe Phe Ser Ser Gly Ala Ser Gln Arg Ile Gln Leu Val
            20                  25                  30

<210> SEQ ID NO 104
<211> LENGTH: 31
<212> TYPE: PRT
```

```
<213> ORGANISM: Hepatitis C virus

<400> SEQUENCE: 104

Ala Thr Tyr Thr Ser Gly Ala Val Ala Ser His Thr Thr Ser Arg Phe
1               5                   10                  15

Thr Ser Leu Phe Ser Ser Gly Ala Ser Gln Arg Ile Gln Leu Val
            20                  25                  30

<210> SEQ ID NO 105
<211> LENGTH: 31
<212> TYPE: PRT
<213> ORGANISM: Hepatitis C virus

<400> SEQUENCE: 105

Ala Thr Tyr Thr Ser Gly Ala Val Ala Ser His Thr Thr Ser Gly Phe
1               5                   10                  15

Thr Ser Leu Phe Ser Ser Gly Ala Ser Gln Arg Ile Gln Leu Val
            20                  25                  30

<210> SEQ ID NO 106
<211> LENGTH: 31
<212> TYPE: PRT
<213> ORGANISM: Hepatitis C virus

<400> SEQUENCE: 106

Glu Thr Tyr Thr Ser Gly Arg Val Ala Gly His Thr Thr Ser Gly Phe
1               5                   10                  15

Thr Ser Leu Phe Ser Ser Gly Ala Ser Gln Arg Ile Gln Leu Val
            20                  25                  30

<210> SEQ ID NO 107
<211> LENGTH: 31
<212> TYPE: PRT
<213> ORGANISM: Hepatitis C virus

<400> SEQUENCE: 107

Ala Thr Tyr Thr Ser Gly Gly Val Ala Gly Arg Thr Thr Ser Gly Phe
1               5                   10                  15

Thr Ser Leu Phe Ser Ser Gly Ala Ser Gln Lys Ile Gln Leu Val
            20                  25                  30

<210> SEQ ID NO 108
<211> LENGTH: 31
<212> TYPE: PRT
<213> ORGANISM: Hepatitis C virus

<400> SEQUENCE: 108

Glu Thr His Thr Thr Gly Arg Val Ala Gly His Thr Thr Ser Arg Phe
1               5                   10                  15

Thr Ser Leu Phe Ser Ser Gly Ala Ser Gln Lys Ile Gln Leu Val
            20                  25                  30

<210> SEQ ID NO 109
<211> LENGTH: 31
<212> TYPE: PRT
<213> ORGANISM: Hepatitis C virus

<400> SEQUENCE: 109

Glu Thr His Thr Thr Gly Arg Val Val Gly His Thr Thr Ser Gly Phe
1               5                   10                  15

Thr Ser Leu Phe Ser Ser Gly Ala Ser Gln Lys Ile Gln Leu Val
            20                  25                  30
```

```
<210> SEQ ID NO 110
<211> LENGTH: 31
<212> TYPE: PRT
<213> ORGANISM: Hepatitis C virus

<400> SEQUENCE: 110

Glu Thr His Thr Thr Gly Arg Val Ala Gly Arg Thr Thr Ser Gly Phe
1               5                   10                  15

Thr Ser Leu Phe Ser Ser Gly Ala Ser Gln Lys Ile Gln Leu Val
            20                  25                  30

<210> SEQ ID NO 111
<211> LENGTH: 31
<212> TYPE: PRT
<213> ORGANISM: Hepatitis C virus

<400> SEQUENCE: 111

Thr Thr Tyr Thr Ser Gly Gly Val Ala Gly Arg Thr Thr Ser Gly Phe
1               5                   10                  15

Thr Ser Leu Phe Ser Ser Gly Ala Ser Gln Lys Ile Gln Leu Val
            20                  25                  30

<210> SEQ ID NO 112
<211> LENGTH: 31
<212> TYPE: PRT
<213> ORGANISM: Hepatitis C virus

<400> SEQUENCE: 112

Lys Thr Tyr Thr Ser Gly Gly Ala Ala Ser His Thr Thr Ser Arg Phe
1               5                   10                  15

Thr Ser Leu Phe Ser Pro Gly Ala Ser Gln Arg Ile Gln Leu Val
            20                  25                  30

<210> SEQ ID NO 113
<211> LENGTH: 31
<212> TYPE: PRT
<213> ORGANISM: Hepatitis C virus

<400> SEQUENCE: 113

Ser Thr Arg Val Thr Gly Gly Gln Gln Gly Arg Ala Val His Gly Ile
1               5                   10                  15

Ala Ser Leu Phe Ser Leu Gly Ala Ser Gln Lys Ile Gln Leu Val
            20                  25                  30

<210> SEQ ID NO 114
<211> LENGTH: 31
<212> TYPE: PRT
<213> ORGANISM: Hepatitis C virus

<400> SEQUENCE: 114

Ser Thr Arg Val Thr Gly Gly Gln Gln Gly Arg Ala Val Gln Gly Phe
1               5                   10                  15

Ala Ser Leu Phe Arg Leu Gly Ala Ser Gln Glu Ile Gln Leu Val
            20                  25                  30

<210> SEQ ID NO 115
<211> LENGTH: 31
<212> TYPE: PRT
<213> ORGANISM: Hepatitis C virus

<400> SEQUENCE: 115
```

Ser Thr Arg Val Thr Gly Gly Gln Gln Gly Arg Ala Val His Gly Ile
1               5                   10                  15

Ala Ser Leu Phe Ser Leu Gly Ala Ser Gln Lys Asn Gln Leu Val
            20                  25                  30

<210> SEQ ID NO 116
<211> LENGTH: 31
<212> TYPE: PRT
<213> ORGANISM: Hepatitis C virus

<400> SEQUENCE: 116

Ser Thr Arg Val Thr Gly Gly Gln Gln Gly His Ala Ala His Ser Leu
1               5                   10                  15

Thr Ser Leu Phe Arg Leu Gly Ala Ser Gln Asn Ile Gln Leu Val
            20                  25                  30

<210> SEQ ID NO 117
<211> LENGTH: 31
<212> TYPE: PRT
<213> ORGANISM: Hepatitis C virus

<400> SEQUENCE: 117

Asn Thr Arg Val Thr Gly Gly Arg Gln Gly Arg Ala Ala His Ser Leu
1               5                   10                  15

Thr Ser Leu Phe Ser Pro Gly Ala Ser Gln Asn Ile Gln Leu Val
            20                  25                  30

<210> SEQ ID NO 118
<211> LENGTH: 31
<212> TYPE: PRT
<213> ORGANISM: Hepatitis C virus

<400> SEQUENCE: 118

Gly Thr Arg Val Thr Gly Gly Arg Gln Gly Arg Ala Ala His Ser Leu
1               5                   10                  15

Thr Ser Leu Phe Ser Pro Gly Ala Ser Glu Asn Ile Arg Leu Val
            20                  25                  30

<210> SEQ ID NO 119
<211> LENGTH: 31
<212> TYPE: PRT
<213> ORGANISM: Hepatitis C virus

<400> SEQUENCE: 119

Ser Thr Arg Val Ser Gly Gly Gln Gln Gly Arg Ala Ala His Ser Leu
1               5                   10                  15

Thr Ser Leu Phe Thr Leu Gly Ala Ser Gln Asn Ile Gln Leu Val
            20                  25                  30

<210> SEQ ID NO 120
<211> LENGTH: 31
<212> TYPE: PRT
<213> ORGANISM: Hepatitis C virus

<400> SEQUENCE: 120

Ser Thr His Val Thr Gly Ala Leu Gln Gly Arg Ala Ala Tyr Gly Ile
1               5                   10                  15

Thr Ser Phe Leu Ser His Gly Pro Ser Gln Lys Ile Gln Leu Val
            20                  25                  30

<210> SEQ ID NO 121
<211> LENGTH: 31

<212> TYPE: PRT
<213> ORGANISM: Hepatitis C virus

<400> SEQUENCE: 121

Ser Thr Gln Val Met Gly Gly Gln Gln Gly Arg Ala Ala Tyr Ser Leu
1               5                   10                  15

Ala Ser Leu Leu Ser Pro Gly Ala Asn Gln Lys Ile Gln Leu Val
            20                  25                  30

<210> SEQ ID NO 122
<211> LENGTH: 31
<212> TYPE: PRT
<213> ORGANISM: Hepatitis C virus

<400> SEQUENCE: 122

Ser Thr Gln Val Met Gly Gly Gln Gln Gly Arg Ala Ala Tyr Ser Leu
1               5                   10                  15

Ala Ser Leu Leu Gly Pro Gly Ala Ser Gln Lys Ile Gln Leu Val
            20                  25                  30

<210> SEQ ID NO 123
<211> LENGTH: 31
<212> TYPE: PRT
<213> ORGANISM: Hepatitis C virus

<400> SEQUENCE: 123

Ser Thr Gln Val Met Gly Gly Gln Gln Gly Arg Ala Ala Tyr Ser Leu
1               5                   10                  15

Ala Ser Leu Leu Ser Pro Gly Ala Ser Gln Lys Ile Gln Leu Val
            20                  25                  30

<210> SEQ ID NO 124
<211> LENGTH: 31
<212> TYPE: PRT
<213> ORGANISM: Hepatitis C virus

<400> SEQUENCE: 124

Arg Thr Arg Thr Val Gly Gly Gln Val Gly His Ser Val Arg Gly Phe
1               5                   10                  15

Thr Ser Leu Phe Ser Ala Gly Ser Ala Gln Asn Ile Gln Leu Ile
            20                  25                  30

<210> SEQ ID NO 125
<211> LENGTH: 31
<212> TYPE: PRT
<213> ORGANISM: Hepatitis C virus

<400> SEQUENCE: 125

Gln Thr Arg Thr Val Gly Gly Gln Val Gly His Ser Val Arg Gly Phe
1               5                   10                  15

Thr Ser Leu Phe Ser Ala Gly Ser Ala Gln Asn Ile Gln Leu Ile
            20                  25                  30

<210> SEQ ID NO 126
<211> LENGTH: 31
<212> TYPE: PRT
<213> ORGANISM: Hepatitis C virus

<400> SEQUENCE: 126

Gln Thr Arg Thr Val Gly Gly Gln Val Gly His Ser Val Arg Gly Phe
1               5                   10                  15

Thr Ser Leu Phe Ser Ala Gly Ser Ala Gln Asp Ile Gln Leu Ile 20                  25                  30

<210> SEQ ID NO 127
<211> LENGTH: 31
<212> TYPE: PRT
<213> ORGANISM: Hepatitis C virus

<400> SEQUENCE: 127

Gln Thr Arg Thr Val Gly Gly Gln Val Gly His Ser Val Arg Gly Phe
1               5                   10                  15

Thr Ser Leu Leu Ser Ala Gly Ser Ala Gln Asn Ile Gln Leu Ile
            20                  25                  30

<210> SEQ ID NO 128
<211> LENGTH: 31
<212> TYPE: PRT
<213> ORGANISM: Hepatitis C virus

<400> SEQUENCE: 128

Gln Thr Arg Thr Val Gly Gly Gln Val Gly His Ser Val Arg Gly Leu
1               5                   10                  15

Thr Ser Leu Phe Ser Ala Gly Ser Ala Gln Asn Ile Gln Leu Ile
            20                  25                  30

<210> SEQ ID NO 129
<211> LENGTH: 31
<212> TYPE: PRT
<213> ORGANISM: Hepatitis C virus

<400> SEQUENCE: 129

Gln Thr Arg Thr Val Gly Gly Gln Met Gly His Gly Val Arg Gly Leu
1               5                   10                  15

Thr Ser Leu Phe Ser Ala Gly Ser Ala Arg Asn Ile Gln Leu Ile
            20                  25                  30

<210> SEQ ID NO 130
<211> LENGTH: 31
<212> TYPE: PRT
<213> ORGANISM: Hepatitis C virus

<400> SEQUENCE: 130

Gln Thr His Thr Val Gly Gly Gln Met Gly His Gly Val Arg Gly Leu
1               5                   10                  15

Thr Ser Leu Phe Ser Ala Gly Ser Ala Gln Asn Ile Gln Leu Ile
            20                  25                  30

<210> SEQ ID NO 131
<211> LENGTH: 31
<212> TYPE: PRT
<213> ORGANISM: Hepatitis C virus

<400> SEQUENCE: 131

Gln Thr His Thr Val Gly Gly Gln Met Gly His Gly Val Arg Gly Leu
1               5                   10                  15

Thr Asn Leu Phe Ser Ala Gly Ser Ala Gln Asn Ile Gln Leu Ile
            20                  25                  30

<210> SEQ ID NO 132
<211> LENGTH: 24
<212> TYPE: PRT
<213> ORGANISM: Hepatitis C virus

<400> SEQUENCE: 132

```
Glu Thr His Val Thr Gly Gly Ser Ala Gly His Thr Val Ser Gly Phe
1               5                   10                  15

Val Ser Leu Leu Ala Pro Gly Ala
            20

<210> SEQ ID NO 133
<211> LENGTH: 31
<212> TYPE: PRT
<213> ORGANISM: Hepatitis C virus
<220> FEATURE:
<221> NAME/KEY: misc_feature
<222> LOCATION: (1)..(1)
<223> OTHER INFORMATION: 2-amino heptanoic is butyl alanine

<400> SEQUENCE: 133

Xaa Glu Thr His Val Thr Gly Gly Ser Ala Gly His Thr Val Ser Gly
1               5                   10                  15

Phe Val Ser Leu Leu Ala Pro Gly Ala Lys Gln Asn Val Gln Leu
            20                  25                  30

<210> SEQ ID NO 134
<211> LENGTH: 6
<212> TYPE: PRT
<213> ORGANISM: Hepatitis C Virus
<220> FEATURE:
<221> NAME/KEY: misc_feature
<222> LOCATION: (4)..(5)
<223> OTHER INFORMATION: Xaa is any amino acid

<400> SEQUENCE: 134

Ser Leu Pro Xaa Xaa Gly
1               5
```

CONSERVED MOTIF OF HEPATITIS C VIRUS E2/NS1 REGION

This application is a divisional of application Ser. No. 08/061,699, filed May 12, 1993, now abandoned.

BACKGROUND OF THE INVENTION

1. Technical Field of the Invention

This invention relates generally to the field of hepatitis C virus (HCV) and, more specifically, to the discovery of an immunologically important motif in the E2/NS1 region.

2. Brief Description of Related Art

Hepatitis C virus (HCV) has been identified as the major causative agent of post-transfusion non-A, non-B hepatitis (NANBH). Materials and methods for obtaining the viral genomic sequences are known. See, e.g., PCT Publ. Nos. WO89/04669. WO90/1±1089, and WO90/14436. For general information about HCV, see Houghton et al. (1991), Hepatology 14:381–388.

Molecular characterization of the HCV genome indicates that it is a RNA molecule of positive polarity containing approximately 9,500 nucleotides comprising a long translational open-reading frame (ORF) that could encode a large polypeptide of approximately 3000 amino acids (aa) beginning with the first in-frame methionine codon. A hypervariable domain located at the amino terminus of the putative envelope glycoprotein E2/NS1 (also called E2) has been located, see PCT Publ. No. WO93/016126; Weiner et al. (1991), Virology 180:842–48; Weiner et al (1992), Proc. Natl. Acad. Sci. USA 89:3468–72; Weiner et al. (1992), *Vaccines* 92:303–08, Cold Spring Harbor Laboratory.

As observed for other RNA viruses, there is a substantial fluidity of the HCV genome resulting from an error-prone replicase and the absence of repair mechanisms that operate during DNA replication. Even in a single infected individual, the HCV genome does not exist as a homogeneous species. Rather, it exists as a quasi-species distribution of closely related but nevertheless heterogeneous genomes. Martell et al. (1992), J. Virol. 66:3225–3229. In addition, the process of host selection and adaptation of a rapidly mutating genome has led to the evolution of many distinct (yet still fluid) HCV genotypes. At least four different HCV genotypes can be distinguished according to the actual degree of nucleotide and amino acid relatedness of full length sequences, and additional different genotypes have been identified based on partial sequences. Mori et al. (1992), Biochem. Biophys. Res. Commun. 183:334–342; Chan et al., (1992), J. Gen. Virol. 73:1131; Cha et al. (1992), Proc. Natl. Acad. Sci. USA 89:7144–7148.

SUMMARY OF THE INVENTION

The present invention is directed to novel vaccine strategies for the treatment of HCV infection and assays for the diagnosis of HCV.

The hypervariable region of E2/NS1 (E2HV) between about amino acid 384 to about amino acid 414 is a rapidly evolving region of HCV and appears to be under positive immune selection. The present invention relates to the existence within this subregion of a motif that is immunogenic and conserved with respect to the character of the amino acids. Although the E2HV amino acid sequences need not be identical within this motif, a definite pattern exists. In HCV1, as well as a number of other isolates, this motif is seen at about amino acids 401 to 407. The presence of this motif in an immunogenic polypeptide is detectable by antibody binding.

The discovery of this motif within the E2/NS1 hypervariable region allows for a strategy of producing materials, including polypeptides and antibodies that may be used for treatment of HCV, whether by direct or passive immunization. Additionally, diagnostic methods employing immunoassays or nucleic acid assays are included herein.

Thus, in one aspect of this invention, a method for passively immunizing an individual for treatment of hepatitis C virus (HCV) infection is provided, the method comprising administering to the individual an antibody composition comprising an antibody capable of binding to a motif comprising an amino acid sequence aa1-aa2-aa3-aa4-aa5-aa6 (SEQ ID NO:1)

wherein aa1 is S, G, A, D, K, R or T; aa2 is L, F, I, M or W; aa3 is F or L; aa4 is any amino acid; aa5 is any amino acid; and aa6 is G or A. In a further embodiment, aa7 is present and attached to aa6; aa7 is A, P, or S.

In another aspect of this invention, an antibody capable of recognizing an antigenic determinant is provided, wherein the antigenic determinant comprises the amino acid sequence aa1-aa2-aa3-aa4-aa5-aa6 (SEQ ID NO:1)

wherein aa1 is S, G, A, D, K, R or T; aa2 is L, F, I, M or W; aa3 is F or L; aa4 is any amino acid; aa5 is any amino acid; and aa6 is G or A. In a further embodiment, aa7 is present and attached to aa6; aa7 is A, P, or S.

In a further aspect of this invention, an immunogenic polypeptide is provided comprising a motif characterized by aa1-aa2-aa3-aa4-aa5-aa6 (SEQ ID NO:1)

wherein aa1 is S, G, A, D, K, R or T; aa2 is L, F, I, M or W; aa3 is F or L; aa4 is any amino acid; aa5 is any amino acid; and aa6 is G or A, provided that the motif is not contained within a 31 amino acid sequence of a naturally-occuring E2HV domain of an HCV isolate known as of May 12, 1993. In a further embodiment, aa7 is present and attached to aa6; aa7 is A, P, or S.

In a still further aspect of this invention, a vaccine is provided comprising: (1) at least one immunogenic polypeptide comprising a motif characterized by aa1-aa2-aa3-aa4-aa5-aa6 (SEQ ID NO:1)

wherein aa1 is S, G, A, D, K, R or T; aa2 is L, F, I, M or W; aa3 is F or L; aa4 is any amino acid; aa5 is any amino acid; and aa6 is G or A; and (2) a pharmaceutically acceptable carrier.

In yet another aspect of this invention, a method of treating an individual for HCV infection is provided, the method comprising administering to the individual the vaccine as described above.

In another aspect of this invention, an immunoassay method for detecting anti-hepatitis C virus (HCV) antibodies in biological samples provided, the method comprising: (a) incubating an antibody-containing biological sample suspected of containing anti-HCV antibodies with a probe antigen comprising an immunogenic polypeptide as described above to permit the formation of an antibody-antigen complex; and (b) detecting the antibody-antigen complex containing the probe antigen.

BRIEF DESCRIPTION OF THE DRAWINGS

FIGS. 2A and 2B show the E2HV sequences for 90 HCV isolates (SEQ. IDS. No. 8–98). The SEQ ID NOS for each E2HV sequence of HCV isolates are (starting from line 1) SEQ ID NO: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, and 98.

FIG. 3 shows the HCV E2HV sequence data from patients followed sequentially after HCV infection (SEQ. IDS. No. 99–131). The SEQ ID NOS for each HCV E2HV sequence are (starting from line 1) SEQ ID NO: 99, 100, 101, 102, 103, 104, 105, 106, 107, 108, 109, 110, 111, 112, 113, 114, 115, 116, 116, 117, 117, 118, 119, 120, 121, 122, 123, 124, 125, 126, 127, 128, 129, 130, and 131.

FIG. 4 shows the percent of conservation for each amino acid at positions 384 to 407 of E2HV.

FIGS. 7A–7C (SEQ. ID. No. 133) present bar graphs of epitope mapping showing the binding of human serum albumin, prealbumin, and TBG to overlapping peptides of the E2HV region. The SEQ ID NO for the sequence recited is SEQ ID NO: 133.

DETAILED DESCRIPTION OF THE INVENTION

A. Definitions

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N. Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory); Methods in Enzymology Vol. 154 and Vol. 155 (Wu and Grossman, and Wu, eds., respectively); Mayer and Walker, eds. (1987), IMMUNOCHEMICAL METHODS IN CELL AND MOLECULAR BIOLOGY (Academic Press, London); Scopes, (1987), PROTEIN PURIFICATION: PRINCIPLES AND PRACTICE, Second Edition (Springer-Verlag, N.Y.); and HANDBOOK OF EXPERIMENTAL IMMUNOLOGY, VOLUMES I–IV (D. M. Weir and C. C. Blackwell eds 1986).

Standard abbreviations for nucleotides and amino acids are used in this specification. All publications, patents, and patent applications cited herein are incorporated by reference.

Figure 1:
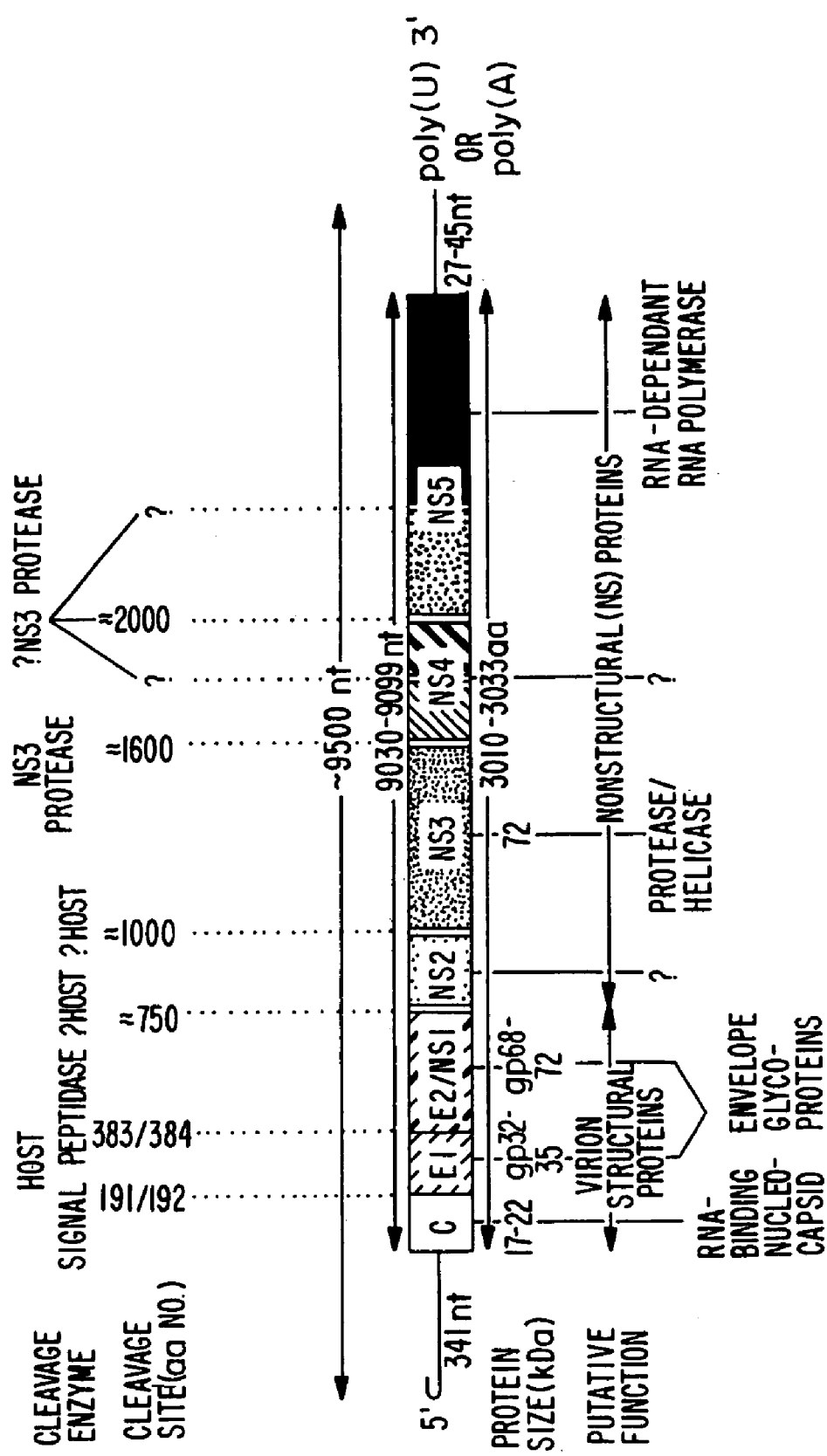
FIG. 1 is a schematic of the genetic organization of HCV.

Hepatitis C virus (HCV) is a new member of the Family Flaviviridae, which includes the pestiviruses (hog cholera virus and bovine diarrhea virus) and the flaviviruses, examples of which are dengue and yellow fever virus. A scheme of the genetic organization of HCV is shown in FIG. 1. Similar to the flavi- and pestiviruses, HCV appears to encode a basic polypeptide domain ("C") at the N-terminus of the viral polyprotein followed by two glycoprotein domains ("E1," "E2/NS1") upstream of the nonstructural genes NS2 through NS5. The amino acid coordinates of the putative protein domains are shown in Table 1.

TABLE 1

| The Putative Protein Domains in HCV | |
|---|---|
| aa coordinates (approximate) | Protein |
| 1–191 | C |
| 192–383 | E1 |
| 384–750 | E2/NS1 |
| 751–1026 | NS2 |
| 1027–1488 | NS3 |
| 1489–1959 | NS4 |
| 1960–3011 | NS5 |

Because the E1 and E2/NS1 regions of the genome encode putative envelope type glycoproteins, these regions are of particular interest with respect to immunogenicity and treatment of HCV.

The average rate of change of the HCV genome within a single persistently-infected individual has been estimated to be $1-2 \times 10^{-3}$ nt changes per site per year. However, there is a much higher rate of change at the extreme 5'-terminus of the gene encoding the N-terminus of the E2/NS1 glycoprotein. Weiner et al., in *Frontiers in virology: Diagnosis of human viruses by polymerase chain reaction technology* (Springer Verlag, Heidelberg, 1992). This E2 hypervariable region (E2HV) spanning amino acids about 384–414 (using HCV1 as a standard for amino acid numbering) (previously named Region V, see, for example, Ogata et al. (1991), Proc. Natl. Acad. Sci. USA 88:3392–3396); Okamoto et al. (1992), Virology 188:331–341) appears to be the most variable region of the HCV polyprotein and is different in virtually every isolate studied so far. Weiner et al. (1992), Proc. Natl. Acad. Sci. USA 89:3468–3472. A number of distinct antibody-binding epitopes have been mapped to this region and in one chronically-infected patient, the emergence of an E2HV variant has been documented, suggesting that escape mutants in this E2HV region may play an important role in the development of chronicity.

As used herein, a "variable domain" of a viral protein is a domain that demonstrates a consistent pattern of amino acid variation between at least two HCV isolates or subpopulations. Preferably, the domain contains at least one epitope. Variable domains can vary from isolate to isolate by as little as one amino acid change. These isolates can be from the same or different HCV group(s) or subgroup(s). Variable domains can be readily identified through sequence composition among isolates, and examples of these techniques are described below. For the purposes of describing the present invention, variable domains will be defined with respect to the amino acid number of the polyprotein encoded by the genome of HCV1, with the initiator methionine being designated position 1. The corresponding variable domain in another HCV isolate is determined by aligning the two isolates sequences in a manner that brings the conserved domains outside any variable domain into maximum alignment. This can be performed with any of a number of computer software packages, such as ALIGN 1.0, available from the University of Virginia, Department of Biochemistry (Attn: Dr. William R. Pearson). See Pearson et al., (1988) Proc. Natl. Acad. Sci. USA 85:2444–2448. It is to be understood that the amino acid numbers given for a particular variable domain are somewhat subjective and a matter of choice. Thus, the beginning and end of variable domains should be understood to be approximate and to include overlapping domains or subdomains, unless otherwise indicated.

"Hypervariable domains" (HV) are variable domains exhibiting relatively high degrees of variability between isolates. In particular, the hypervariable region of HCV E2/NS1, referred to herein as E2HV, spans amino acids 384–414.

The present invention utilizes a region within E2HV of E2/NS1 that has a conserved motif of amino acids, referred to herein as the "SLF-G" (SEQ ID NO:134) motif for either amino acids 401 to 406 or from amino acids 401 to 407. This region was discovered by analysis of sequences of 90 isolates that encompass at least four genotypes of HCV. Antibody preparations comprised of antibodies that bind to the region with the conserved motif are useful for passive immunization against HCV.

It is of course understood that the amino acids may be substituted with other molecules, for example, analogs of these amino acids, so long as the characteristics of the motif with respect to immunoreactivity are maintained. The immunoreactivity of an antigenic determinant as compared to that of one comprised of the SLF-G (SEQ ID NO:134) motif is determinable by one of ordinary skill in the art using routine methods. For example, known methods include those used for epitope mapping, as well as competitive binding to antibodies that are immunologically reactive (bind) with antigenic determinants containing the motif.

As used herein, the term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

Polypeptides useful in the manufacture of the compositions of the present invention can be made recombinantly, synthetically, or in tissue culture. Recombinant polypeptides comprised of the truncated HCV sequences or full-length HCV proteins can be made up entirely of HCV sequences (one or more epitopes, either contiguous or noncontiguous) or sequences in a fusion protein. In fusion proteins, useful heterologous sequences include sequences that provide for secretion from a recombinant host, enhance the immunological reactivity of the HCV epitope(s) or facilitate the coupling of the polypeptide to a support or a vaccine carrier. See, e.g., EPO Publ. No. 116,201; U.S. Pat. No. 4,722,840; EPO Publ. No. 259,149; U.S. Pat. No. 4,629,783.

A significant advantage of producing the protein by recombinant DNA techniques rather than by isolating and purifying a protein from natural sources is that equivalent quantities of the protein can be produced by using less starting material than would be required for isolating the protein from a natural source. Producing the protein by recombinant techniques also permits the protein to be isolated in the absence of some molecules normally present in cells. Indeed, protein compositions entirely free of any trace of human protein contaminants can readily be produced because the only human protein produced by the recombinant nonhuman host is the recombinant protein at issue. Potential viral agents from natural sources and viral components pathogenic to humans are also avoided.

Polypeptides comprised of the SLF-G (SEQ ID NO:134) motif may be prepared by chemical synthesis. Methods of preparing polypeptides by chemical synthesis are known in the art. The protein may be used for producing antibodies. An "antibody" is any immunoglobulin, including antibodies and fragments thereof (including F(ab), F(ab')2, and Fv) that binds a specific epitope. The term encompasses, inter alia, polyclonal, monoclonal, single-chain, and chimeric antibodies: Examples of chimeric antibodies are discussed in U.S. Pat. Nos. 4,816,397 and 4,816,567.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term-refers only to the primary structure of the *molecule*. T*hus*, this term includes *double*- and *single-stranded* DNA and RNA. I*t* also includes known types of *modifications*, for *example*, labels which are known in the *art*, *methylation*, "*caps*", substitution of one or more of the naturally occurring nucleotides with an *analog*, internucleotide modifications such *as*, for *example*, those with uncharged linkages (*e.g*., methyl *phosphonates*, *phosphotriesters*, *phosphoamidates*, *carbamates*, *etc*.) and with charged linkages (*e.g*., *phosphorothioates*, *phosphorodithioates*, *etc*.), those containing pendant *moieties*, such *as*, for example proteins (*including* for *e.g*., *nucleases*, *toxins*, *antibodies*, signal *peptides*, *poly*-L-*lysine*, *etc*.), those with intercalators (*e.g*., *acridine*, *psoralen*, *etc*.), those containing chelators (*e.g*., *metals*, radioactive *metals*, *boron*, oxidative *metals*, *etc*.), those containing *alkylators*, those with modified linkages (*e.g*., alpha anomeric nucleic *acids*, *etc*.), as well as unmodified forms of the *polynucleotide*.

A "replicon" is any genetic element, e.g., a plasmid, a chromosome, a virus, a cosmid, etc. that behaves as an autonomous unit of polynucleotide replication within a cell; i.e., capable of replication under its own control. This may include selectable markers.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and may also include additional components whose presence is advantageous, for example, leader sequences and fusion partner sequences. A "promoter" is a nucleotide sequence which is comprised of consensus sequences which allow the binding of RNA polymerase to the DNA template in a manner such that mRNA production initiates at the normal transcription initiation site for the adjacent structural gene.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

"PCR" refers to the technique of polymerase chain reaction as described in Saiki, et al., Nature 324:163 (1986); and Scharf et al., Science (1986) 233:1076–1078; and U.S. Pat. No. 4,683,195; and U.S. Pat. No. 4,683,202.

As used herein, x is "heterologous" with respect to y if x is not naturally associated with y in the identical manner; i.e., x is not associated with y in nature or x is not associated with y in the same manner as is found in nature.

"Homology" refers to the degree of similarity between x and y. Homology between two polynucleotide sequences can be determined by techniques known in the art. For example, it can be determined by a direct comparison of the sequence information of the polynucleotide. Alternatively, homology can be determined by hybridization of the polynucleotides under conditions which form stable duplexes between homologous regions (for example, those which would be used prior to $S_1$ digestion), followed by digestion with single-stranded specific nuclease(s), followed by size determination of the digested fragments.

"Recombinant host cells", "host cells," "cells," "cell cultures," and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

Specifically, as used herein, "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells. Preferably, cell lines include nonhybrid cell lines or hybridomas to only two cell types.

As used herein, the term "microorganism" includes prokaryotic and eukaryotic microbial species such as bacteria and fungi, the latter including yeast and filamentous fungi.

"Transformation" refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "genomic" is meant a collection or library of DNA molecules which are derived from restriction fragments that have been cloned in vectors. This may include all or part of the genetic material of an organism.

By "cDNA" is meant a complimentary mRNA sequence that hybridizes to a complimentary strand of mRNA.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

As used herein, "epitope" is a single antigenic determinant which has a structure complementary to the recognition site on a lymphocyte receptor or an antibody. Functionally, it is determined by the ability of an antigen to bind to an antibody in a standard assay. Generally, an epitope comprises at least 3 to 5 amino acids. Sometimes, epitopes can be larger, e.g., 6, 7, 8, 9, or 10 amine acids.

An epitope or antigenic determinant is the equivalent of another epitope or antigenic determinant in a designated polypeptide when it cross-reacts with antibodies which bind immunologically to the epitope or antigenic determinant in the designated polypeptide. Often, these are one or more amino acids within an epitope that are not critical for antibody binding and are thus capable of substitution or even deletion. Although linear epitopes are usually short, contiguous sequences (subject to some change), conformational epitopes can be comprised of a few amino acids widely spaced within the linear amino acid sequence, but brought within close proximity due to folding or other secondary or tertiary structural features of the protein.

An "antigen" is a polypeptide containing one or more antigenic determinants.

"Immunogenic" means the ability to elicit a cellular and/or humoral immune response. An immunogenic response may be elicited by immunogenic polypeptides alone, or may require the presence of a carrier in the presence or absence of an adjuvant.

"Immunoreactive" refers to (1) the ability to bind immunologically to an antibody and/or to a lymphocyte antigen receptor or (2) the ability to be immunogenic.

The amino acid sequence comprising the HCV epitope may be linked to another polypeptide (e.g., a carrier protein), either by covalent attachment or by (expressing a fused polynucleotide to form a fusion protein. If desired, one may insert or attach multiple repeats of the epitope, and/or incorporate a variety of epitopes. The carrier protein may be derived from any source, but will generally be a relatively large, immunogenic protein such as BSA, KLH, or the like. If desired, one may employ a substantially full-length HCV protein as the carrier, multiplying the number of immunogenic epitopes. Alternatively, the amino acid sequence from the HCV epitope may be linked at the amino terminus and/or carboxy terminus to a non-HCV amino acid sequence, thus the polypeptide would be a fusion polypeptide. Analogous types of polypeptides may be constructed using epitopes from other designated viral proteins.

An "individual" refers to a vertebrate, particularly a member of a mammalian species, and includes but is not limited to rodents (e.g., mice, rats, hamsters, guinea pigs), rabbits, goats, pigs, cattle, sheep, and primates (e.g., chimpanzees, African Green Monkeys, baboons, orangutans, and humans).

As used herein, "treatment" refers to any of (i) the prevention of infection or reinfection, as in a traditional vaccine, (ii) the reduction or elimination of one or more symptoms associated with an HCV infected state, and (iii) the substantial or complete elimination of the virus. Treatment may be effected prophylactically (prior to infection) or therapeutically (following infection).

As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumors, organs, biopsies and also samples of in vitro cell culture constituents (including but not limited to conditioned medium resulting from the growth of cells in cell culture medium, e.g., Mab producing myeloma cells, recombinant cells, and cell components).

An "immune response" to a composition or vaccine is the development in the host of a cellular and/or antibody-mediated immune response to the intracellular infectious agent that encodes the target antigen. Usually, such a response comprises the individual producing cytotoxic T cells and/or B cells and/or a variety of classes of T cells directed specifically to antigen presenting cells expressing the target antigen.

B. Expression Systems

The availability of DNA sequences encoding the polypeptides of this invention permits the construction of expression vectors encoding these polypeptides. The DNA encoding the desired polypeptide, whether in fused or mature form, and whether or not containing a signal sequence to permit secretion, may be ligated into expression vectors suitable for any convenient host. Both eukaryotic and prokaryotic host systems are presently used in forming recombinant polypeptides, and a summary of some of the more common control systems and host cell lines is given below. The polypeptide is then isolated from lysed cells or from the culture medium and purified to the extent needed for its intended use. Purification may be by techniques known in the art, for example, differential extraction, salt fractionation, chromatography on ion exchange resins, affinity chromatography, centrifugation, and the like. See, for example, Methods in Enzymology (Academic Press) for a variety of methods for purifying proteins. Such polypeptides can be used as diagnostics, or those which give rise to neutralizing antibodies may be formulated into vaccines. Antibodies raised against these polypeptides can also be used as diagnostics, or for passive immunotherapy.

Both prokaryotic and eukaryotic host cells may be used for expression of desired coding sequences when appropriate control sequences which are compatible with the designated host are used. Methods for such expression are known in the art. Among prokaryotic hosts, E. coli is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the B-lactamase (penicillinase) and lactose promoter systems (Chang et al. (1977) Nature 198:1056.), the tryptophan (trp) promoter system (Goeddel et al. (1980) Nucleic Acids Res. 8:4057) and the lambda-derived $P_L$ promoter and N gene ribosome binding site (Shimatake et al. (1981) Nature 292:128) and the hybrid tac promoter (De Boer et al. (1983) Proc. Natl. Acad. Sci. USA 292:128) derived from sequences of the trp and lac UV5 promoters. The foregoing systems are particularly compatible with E. coli; if desired, other prokaryotic hosts such as strains of Bacillus or Pseudomonas may be used, with corresponding control sequences.

Eukaryotic hosts include yeast and mammalian cells in culture systems. Saccharomyces cerevisiae and Saccharomyces carlsbergensis are the most commonly used yeast hosts, and are convenient fungal hosts. Yeast compatible vectors carry markers which permit selection of successful transformants by conferring prototrophy to auxotrophic mutants or resistance to heavy metals on wild-type strains. Yeast compatible vectors may employ the 2μ origin of replication (Broach et al. (1983) Meth. Enz. 101:307), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al. (1968) J. Adv. Enzyme Reg 7:149; Holland et al. (1978) Biochemistry 17:4900), including the promoter for 3 phosphoglycerate kinase (Hitzeman (1980) J. Biol. Chem. 255:2073). Terminators may also be included, such as those derived from the enolase gene (Holland (1981) J. Biol. Chem. 256: 1385). Particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, leader sequence from yeast α-factor. In addition, the transcriptional regulatory region and the transcriptional initiation region which are operably linked may be such that they are not naturally associated in the wild-type organism. These systems are described in detail in EPO 120,551, published Oct. 3, 1984;

EPO 116,201, published Aug. 22, 1984; and EPO 164,556, published Dec. 18, 1985, all of which are assigned to the herein assignee, and are hereby incorporated herein by reference.

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40) (Fiers (1978) Nature 273:113), Rous sarcoma virus (RSV), adenovirus (ADV), and bovine papilloma virus (BPV). Mammalian cells may also require terminator sequences and poly-A addition sequences; enhancer sequences which increase expression may also be included, and sequences which cause amplification of the gene may also be desirable. These sequences are known in the art.

Vectors suitable for replication in mammalian cells are known in the art, and may include viral replicons, or sequences which insure integration of the appropriate sequences encoding NANBV epitopes into the host genome.

A vector which is used to express foreign DNA, and which may be used in vaccine preparation is Vaccinia virus. In this case the heterologous DNA is inserted into the Vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid vectors that greatly facilitate the construction of recombinant viruses have been described (see, for example, Mackett et al. (1984) J. Virol. 49:857: Chakrabarti et al. (1985) Mol. Cell Biol. 5:3403; Moss (1987) in GENE TRANSFER VECTORS FOR MAMMALIAN CELLS (Miller and Calos, eds., Cold Spring Harbor Laboratory, Cold Spring Harbor, N.Y.), p. 10.). Expression of the HCV polypeptide then occurs in cells or individuals which are immunized with the live recombinant vaccinia virus.

Other systems for expression of eukaryotic or viral genomes include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector for use in *Spodoptera frugiperda* cells in culture, for example. Expression vectors derived from this system usually use the strong viral polyhedrin gene promoter to drive expression of heterologous genes. Currently the most commonly used transfer vector for introducing foreign genes into AcNPV is pAc373 (FIG. 70). Many other vectors, known to those of skill in the art, have also been designed for improved expression. These include, for example, pVL985 (which alters the polyhedrin start codon from ATG to ATT, and which introduces a BamHI cloning site-32 basepairs downstream from the ATT; See Luckow and Summers (1989) Virology 17:31.).

Methods for the introduction of heterologous DNA into the desired site in the baculovirus virus are known in the art. (See Summer and Smith, Texas Agricultural Experiment Station Bulletin No. 1555; Smith et al. (1983) Mol. & Cell Biol. 3:2156–2165.; and Luckow and Summers (1989)). For example, the insertion can be into a gene such as the polyhedrin gene, by homologous recombination; insertion can also be into a restriction enzyme site engineered into the desired baculovirus gene.

C. Vaccine Treatment of HCV

In one embodiment of the invention, the immunogenic compositions comprised of a polypeptide having a region that binds an antibody directed to a antigenic determinant containing the SLF-G (SEQ ID NO:134) motif is used for vaccine applications to stimulate immune responsiveness to the HCV antigenic determinant(s) containing the motif. Preferably, the polypeptides do not contain the specific E2HV sequences disclosed in PCT Publ. No. WO93/016126; Weiner et al. (1991), Virology 180:842–48; Weiner et al (1992), Proc. Natl. Acad. Sci. USA 89:3468–72; Weiner et al. (1992), Vaccines 92:303–08, Cold Spring Harbor Laboratory.

Preliminary evidence suggests that the hypervariable domain(s) of E2/NS1 may be responsible for escape mutants, leading to chronic HCV infections. However, a conserved region within the hypervariable region is suggestive that the conserved region has an important function and plays an essential role in virus binding and/or entry into and/or replication in the host cell. In virus binding it is contemplated that the binding may be to the cell and/or to another molecule which facilitates virus binding and/or entry and/or replication. The examples presented infra are suggestive that virus binding to transthyretin and/or to thyroid binding globulin (TBG) are involved in the infective process. Thus, increasing an immune response to antigenic determinants containing the conserved SLF-G (SEQ ID NO:134) sequence may lead not only to protection against and/or alleviation of HCV infection, but also to a reduction in chronicity of HCV infection. In addition, the conserved region is also suggestive that the vaccines comprised of the immununoreactive polypeptides having a region with the SLF-G (SEQ ID NO:134) motif may be cross-reactive.

In preferred applications for vaccines, the polypeptide compositions described herein are combined with other HCV subunit antigens, for example, those described in PCT Publ. No. WO92/08734. In cases where the composition is to be used for treatment of HCV, it is desirable that the composition be immunogenic. In instances wherein the synthesized polypeptide is correctly configured so as to provide the correct epitope, but is too small to be immunogenic, the polypeptide may be linked to a suitable carrier. A number of techniques for obtaining such linkage are known in the art, including the formation of disulfide linkages using N-succinimidyl-3-(2-pyridyl-thio)propionate (SPDP) and succinimidyl 4-(N-maleimidomethyl)cyclohexane-1-carboxylate (SMCC) (if the peptide lacks a sulfhydryl group, this can be provided by addition of a cysteine residue.) These reagents create a disulfide linkage between themselves and peptide cysteine resides on one protein and an amide linkage through the e-amino on a lysine, or other free amino group in other amino acids. A variety of such disulfide/amide-forming agents are known. See, for example, Immun. Rev. (1982) 62:185. Other bifunctional coupling agents form a thioether rather than a disulfide linkage. Many of these thio-ether-forming agents are commercially available and include reactive esters of 6-maleimidocaproic acid, 2-bromoacetic acid, 2-iodoacetic acid, 4-(N-maleimido-methyl)cyclohexane-1-carboxylic acid, and the like. The carboxyl groups can be activated by combining them with succinimide or 1-hydroxyl-2-nitro-4-sulfonic acid, sodium salt. Additional methods of coupling antigens employ the rotavirus/ "binding peptide" system described in EPO Publ. No. 259, 149. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysaccharides such as latex functionalized sepharose, agarose, cellulose, cellulose beads and the like; polymeric amino acids, such as polyglutamic acid, polylysine, and the like; amino acid copolymers; and inactive virus particles (see infra.). Especially useful protein substrates are serum albumins, keyhole limpet hemocyanin, immunoglobulin molecules, thyroglobulin, ovalbumin, tetanus toxoid, and other proteins well known to those of skill in the art.

The immunogenicity of the antigens comprised of the SLF-G (SEQ ID NO:134) motif may also be enhanced by preparing them in eukaryotic systems fused with or assembled with particle-forming proteins such as, for example, that associated with hepatitis B surface antigen. See, e.g., U.S. Pat. No. 4,722,840. These constructs may also be expressed in mammalian cells such as CHO cells using an SV40-dihydrofolate reductase vector (Michelle et al. (1984)).

In addition, portions of the particle-forming protein coding sequence may be replaced with codons encoding the SLF-G (SEQ ID NO:134) epitope from an HCV hypervariable domain. In this replacement, regions which are not required to mediate the aggregation of the units to form immunogenic particles in yeast or mammals can be deleted, thus eliminating additional HBV antigenic sites from competition with the HCV epitope(s).

These vaccines may either be prophylactic (to prevent infection) or therapeutic (to treat disease after infection).

Such vaccines comprise antigen or antigens, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5 Tween® 80 (sorbitan monooleate), and 0.5% Span® 85 sorbitan trioleate, optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween® 80 (sorbitan monooleate), 5% pluronic® L121 methyl oxirane, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween® 80 (sorbitan monooleate), and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon® (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc; and (6) other substances that act as immunostimulating agents to enhance the effectiveness of the composition. Alum and MF59 are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycerohydroxyphosphoryloxy)-ethylamine (MTP-PE), etc.

The immunogenic compositions (e.g., the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic polypeptides, as well as any other of the above-mentioned components, as needed. "Immunologically effective amount" means that the administration of that amount to an individual, either in a single dose or as part of a series, is effective for treatment. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

In addition to the above, it is also possible to prepare live vaccines of attenuated microorganisms which express recombinant polypeptides comprised of a region with the SLF-G (SEQ ID NO:134) motif. Suitable attenuated microorganisms are known in the art and include, for example, viruses (e.g., vaccinia virus) as well as bacteria.

In addition, the vaccine containing the with an antigenic determinant comprised of the conserved motif SLF-G (SEQ ID NO:134) may be administered in conjunction with other immunoregulatory agents, for example, immune globulins.

D. Antibodies

In another embodiment of the invention, the immunogenic polypeptides prepared as described above are used to produce antibodies, including polyclonal and monoclonal. If polyclonal antibodies are desired, a selected mammal (e.g., mouse, rabbit, sheep, goat, horse, etc.) is immunized with an immunogenic polypeptide bearing an HCV epitope(s). Serum from the immunized animal is collected and treated according to known procedures. If serum containing polyclonal antibodies to antigenic determinant(s) comprised of the SLF-G (SEQ ID NO:134) motif contains antibodies to other antigens, the polyclonal antibodies can be purified by immunoaffinity chromatography. Techniques for producing and processing polyclonal antisera are known in the art, see for example, Mayer and Walker (1987).

Alternatively, polyclonal antibodies may be isolated from a mammal which has been previously infected with HCV, and antibodies directed to antigenic determinant(s) comprised of the SLF-G- (SEQ ID NO:134) motif isolated. Monoclonal antibodies directed against HCV epitopes can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980); Hammerling et al. (1981); Kennett et al. (1980); see also, U.S. Pat. Nos. 4,341,761; 4,399,121; 4,427,783; 4,444,887; 4,466,917; 4,472,500; 4,491,632; and 4,493,890. Panels of monoclonal antibodies produced against HCV epitope(s) comprised of the SLF-G (SEQ ID NO:134) motif can be screened for various properties; i.e., for isotype, epitope affinity, etc.

Antibodies, both monoclonal and polyclonal, which are directed against HCV epitope(s) comprised of the SLF-G (SEQ ID NO:134) motif are particularly useful in diagnosis, and those which are neutralizing are useful in passive immunotherapy. Monoclonal antibodies, in particular, may be used to raise anti-idiotype antibodies.

Anti-idiotype antibodies are immunoglobulins which carry an "internal image" of the antigen of the infectious agent against which protection is desired. See, for example, Nisonoff, A., et al. (1981) and Dreesman et al. (1985). Techniques for raising anti-idiotype antibodies are known in the art. See, for example, Grzych (1985), MacNamara et al. (1984), and Uytdehaag et al. (1985). These anti-idiotype antibodies may also be useful for treatment, vaccination and/or diagnosis of HCV infection, as well as for an elucidation of the immunogenic region(s) of HCV antigens comprised of the SLF-G (SEQ ID NO:134) motif.

E. Passive Immunization

In another embodiment of the invention, compositions comprised of neutralizing antibodies directed to an antigenic determinant(s) comprised of the SLF-G (SEQ ID NO:134) motif are used for passive immunization of individuals for prophylaxis and/or therapy of HCV infection. If the antibodies are polyclonal, it is preferable to fractionate the antibody preparations prior to administration in order to separate and concentrate active fractions, for example, inter alia, IgGs and IgMs. Techniques for separating various fractions of antibodies are known by those of skill in the art, and require only routine methods. If monoclonal antibodies are used for passive immunization, it may be preferable to include a variety of monoclonal antibodies directed to one or more HCV antigenic determinants as well as the antibodies directed to the antigenic determinant(s) comprised of the SLF-G (SEQ ID NO:134) motif.

Methods and protocols for passive immunization are known in the art, and are discussed in several of the references cited above. Generally, the antibodies are mixed with suitable excipients. The antibodies may be given in single or multiple doses, and in effective amounts. Generally, because of differences between individuals to which the antibodies are administered, the dosage and regimen is determined by the person supervising the administration.

F. Diagnostic Assays

For diagnostic application, it may be useful to employ the compositions of the present invention as antigens, thereby improving the ability to detect antibody to various HCV isolates. Typically the polypeptides can be used directly in a homogeneous or heterogeneous immunoassay format, the latter preferably comprising immobilizing the polypeptide on a solid substrate (e.g., microtiter plate wells, plastic beads, nitrocellulose, etc.). See, e.g., PCT Publ. No. WO90/11089; EPO Publ. No. 360,088; IMMUNOASSAY: A PRACTICAL GUIDE, supra. These immunogenic compositions comprised of a polypeptide containing a region with the SLF-G (SEQ ID NO:134) motif are used to detect anti-HCV antibodies within biological samples, including for example, blood or serum samples. The immunoassay will use least one antigen with an antigenic determinant comprised of the SLF-G (SEQ ID NO:134) motif. It is also contemplated that antibodies directed to antigenic determinants comprised of the SLF-G (SEQ ID NO:134) motif may be used to detect antigens with the motif in biological samples. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention in suitable containers, along with the remaining reagents and materials (for example, suitable buffers, salt solutions, etc) required for the conduct of the assay, as well as a suitable set of assay instructions.

G. Gene Therapy

In another embodiment of the invention polynucleotides encoding immunogenic polypeptides comprised of the SLF-G (SEQ ID NO:134) motif are used for purposes of gene therapy for individuals to prevent and/or alleviate HCV infections. The sequence encoding the immunogenic polypeptide containing a region comprised of the SLF-G (SEQ ID NO:134) motif is operably linked to a transcriptional control region. Transcriptional control regions are known in the art.

In some embodiments of the invention, the transcriptional control regions may be hybrids, including enhancer regions, multimeric transcription factor binding sites (e.g., NF-AT and/or NFKB), secretion signals, or positive markers that enable the selection of cells carrying the recombinant polynucleotide.

Polynucleotide constructs prepared for introduction into a prokaryotic or eukaryotic host cell for replication may comprise a replication system recognized by the host, including the intended recombinant polynucleotide fragment encoding the desired polypeptide. Such vectors may be prepared by means of standard recombinant techniques well known in the art and discussed, for example, in Sambrook et al. (1989) or Ausubel et al (1987).

The recombinant polynucleotides encoding the polypeptides of the invention may be introduced into individuals in several ways. For example, the polynucleotides may be introduced ex vivo into a host cell, for example, dendritic cells, or cells from a skin biopsy. The cells containing the recombinant polynucleotide may be used to confer immunity to individuals. The cells are usually administered by infusion, with each infusion in a range of at least $10^6$ to $10^{10}$ cells/m$^2$, preferably in the range of at least $10^7$ to $10^9$ cells/m$^2$. The clones may be administered by a single infusion, or by multiple infusions over a range of time. However, since different individuals are expected to vary in responsiveness, the type and amount of cells infused, as well as the number of infusions and the time range over which multiple infusions are given are determined by the attending physician or veterinarian, and can be determined by routine examination.

The polynucleotides encoding the immunogenic polypeptides comprised of the SLF-G (SEQ ID NO:134) motif may be introduced into the desired cell ex vivo by means known in the art, including, for example, transformation, electroporation, lipofection, and transduction, including the use of adeno-associated viral (AAV) vectors, and particularly using methods of retroviral gene transfer known in the art.

Various infection techniques known in the art have been developed which utilize recombinant infectious virus particles for gene delivery. Retroviral vectors provide a highly efficient method for gene transfer into eukaryotic cells. Numerous retroviral vector constructs have been used successfully to express many foreign genes (see, e.g., Cofin, in Weiss et al. (eds.), RNA Tumor Viruses, 2nd ed., vol. 2 (Cold Spring Harbor Laboratory, New York, 1985, pp. 17–71).

In other embodiments of the invention, the recombinant polynucleotides encoding the immunogenic polypeptides containing the SLF-G (SEQ ID NO:134) motif are introduced directly into the individual to be treated and/or immunized. In these embodiment it is preferred that the polynucleotide be in the form of an expression vector, and even more preferably a circular plasmid. The polynucleotides are mixed with suitable excipients, and administered to the individual by any suitable means known in the art, including, for example parenteral (including, for example, intravenous, intraperitoneal, intramuscular, and subcutaneous) ingestion, lipofection, and transdermal.

EXAMPLES

Described below are examples provided only for illustrative purposes and not to limit the scope of the present invention. In light of the present disclosure, numerous embodiments within the scope of the claims will be apparent to those of ordinary skill in the art.

Example 1

Identification of a Conserved Motif in E2HV

A conserved motif(s) within the E2HV domain was identified by examining 90 E2HV sequences from isolates from around the world for conserved features. The HCV sequences examined are shown in FIGS. 2A and 2B. The examination showed significant variability of the E2HV sequences.

E2HV sequence data from patients followed sequentially after HCV infection is indicative that mutations appear with greater frequency between amino acids 395 to 407 and with time appear throughout the remainder of the E2HV domain. See FIG. 3, which presents the sequence data for three patients: Hutchinson (H) (Ogata et al. (1991), Proc. Natl. Acad. Sci. USA 88:3392–3396); HC-J4 (Okamoto et al. (1992), Virology 188:331–341); and NY/RS (Kato et al. (1992), Biochem. Biophys. Res. Commun. 181:279–285).

It is also observed from FIG. 3 that Patient RS appears to have a different pattern of fewer, randomly distributed point mutations acumulating over time. The RS pattern of amino acid substitutions has been observed in a subset of HCV infected patients and in a chronically infected chimpanzee (See, for example, Weiner et al., Vaccines 92, supra.) An explanation for the difference in the pattern of mutations accumulated with time in patients RS and NY, for example, is that individuals such as RS fail to make antibodies to the E2HV epitope(s). In the absence of positive immune selection, the sequence mutates randomly as a quasispecies distribution of HCV variants evolves. The chronically infected chimpanzee, who had a poor immune response to HCV antigens, showed a similar pattern of E2HV mutations as patient RS.

The results of the examination of sequences is shown in FIG. 4, which shows the degree of conservation of character of amino acids 384 to 407. Although no two E2HV sequences are identical, amino acids 401 to 403 and 406 to 407 are strongly conserved for the characteristics of the amino acids at those positions. Amino acid 401 is S, G, A, D, K, R, or T; amino acid 402 is L, F, I, M, or W; amino acid 403 is. F or L; amino acid 406 is G or A; amino Acid 407 is A, P, or S. The relative prevalence of the amino acids in these positions in the 90 sequences examined is shown in Table 2.

TABLE 2

Summary of Amino Acid Substitutions in the E2HV Conserved Motif

| S aa401 | L aa402 | F aa403 | G aa406 | A/P/S aa407 |
|---|---|---|---|---|
| 62 S | 68 L | 77 F | 89 G | 45 A |
| 18 G | 12 F | 13 L | 1 A | 35 P |
| 2 A | 6 I | | | 10 S |
| 2 T | 3 M | | | |
| 1 D | 1 W | | | |
| 1 K | | | | |
| 4 R | | | | |

Example 2

Mapping of HCV1 E2HV Epitopes

For epitope mapping of the E2HV region of E1/NS1, see PCT Publ. No. WO93/00365, with the following modifications. Overlapping peptides from the sequence spanning amino acid positions 384 to 413 of HCV1 attached to pins were prepared. The peptides were reacted with an IgG preparation from sheep that had been immunized with a conjugated 30-mer peptide from the same region.

The sheep IgG preparations containing anti-HV E2 antibodies were prepared from sheep immunized with a peptide coupled to diphtheria toxoid. The peptide spanned the HCV1 E2HV region, and had the following sequence:

acetyl-C-B-E-T-H-V-T-G-G-S-A-G-H-T-V-S-G-F-V-S-L-L-A-P-G-A-K-Q-N-V-Q-L-acid (SEQ ID NO:2) wherein B is butyl alanine.

Figure 5A:
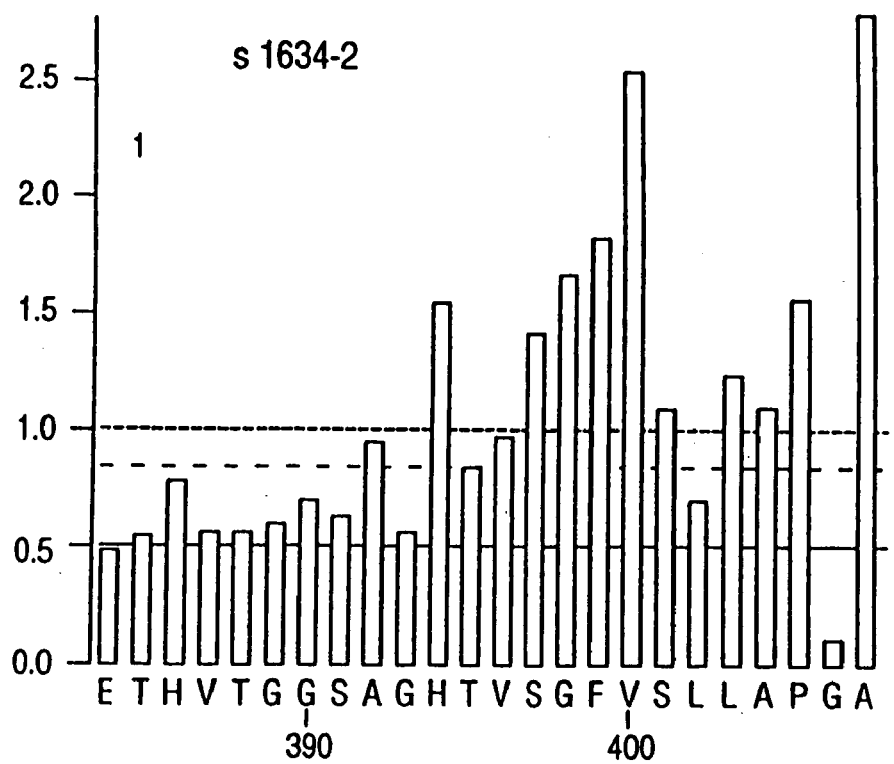
FIGS. 5A (SEQ. ID. No. 132) and 5B (SEQ. ID. No. 132) present bar graphs of epitope mapping showing the binding of serum from sheep immunized with a peptide that spanned the HCV1 E2HV region to 8-mer overlapping mimotopes that spanned the same region. The SEQ ID NO for the sequence recited is SEQ ID NO: 132.
Figure 5B:
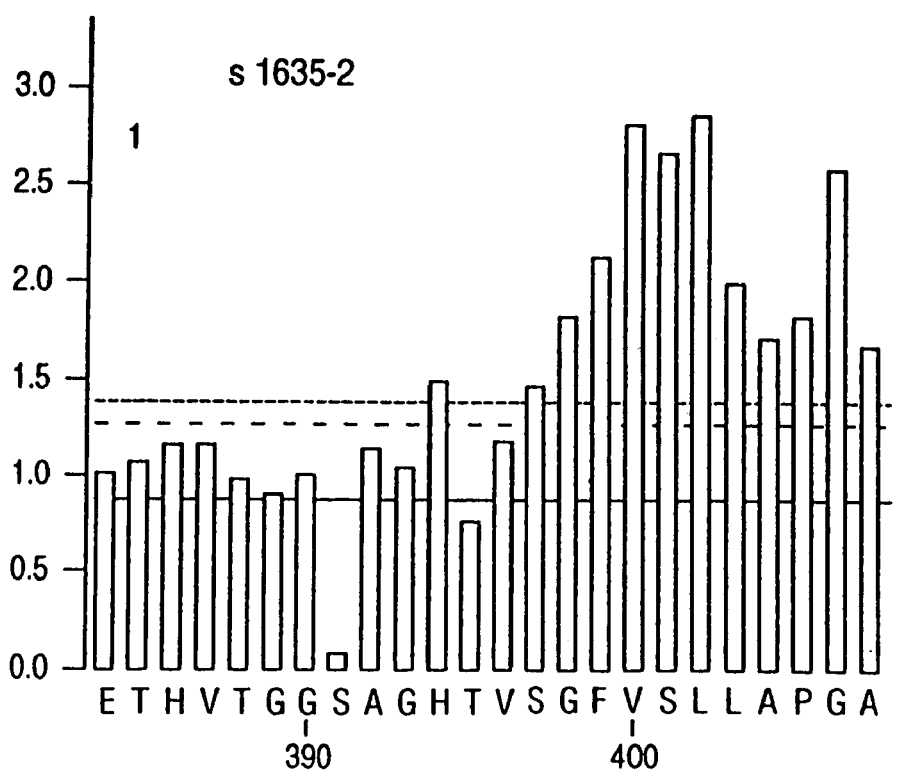

The results of the screening using sheep serum IgG s1634-2 and s1635-2 from sheep immunized with the conjugated 30-mer are shown in FIGS. 5A and 5B. The results indicate that sheep 1634-2 IgG reacts with the minimum epitope $^{400}$VSLLA$^{404}$ (SEQ. ID. NO: 3). IgG from sheep 1635-2 has a broader reactivity profile—the sera reacts with the peptides containing the minimum $^{400}$VSLLA$^{404}$ (SEQ. ID. NO: 3) epitope, and in addition peptides containing the minimum epitopes $^{401}$SLLAPGA$^{407}$ (SEQ. ID. NO: 4) and $^{403}$LAPGA$^{407}$ (SEQ. ID. NO: 5). Thus, the IgG preparation from sheep immunized with the 30-mer peptide of E2HV is reactive with linear epitope(s) between amino acids 400 to 407.

Within the conserved region of E2HV, the sequence of the conserved motif of HCV1 is S-L-L-aa4-aa5-G-(A/P/S) (SEQ ID NO:6). The substitution of L for F in the motif S-L-F-aa4-aa5-G-(A/P/S) (SEQ ID NO:7) motif is conservative with respect to the amino acid characteristics.

The methods used in this example are described below.

Synthesis of Overlapping Peptides

The synthesis of the overlapping peptides was as follows. Specially prepared and derivatized polyethylene pins arranged on a block in an 8×12 array (Coselco Mimotopes, Victoria, Australia) were prepared by placing the pins in a bath (20% v/v piperidine in dimethylormamide (DMF)) for 30 minutes at room temperature. The pins were then removed, washed in DMF for 5 min, then washed in methanol four times (2 min/wash). The pins were allowed to air dry for at least 10 min, then washed a final time in DMF (5 min). 1-Hydroxybenzotriazole (HOBt, 367 mg) was dissolved in DMF (80 ml) for use in coupling Fmoc-protected amino acids: Fmoc-L-Ala-OPfp, Fmoc-L-Cys(Trt)-Opfp, Fmoc-L-Asp(O-tBu)-OPfp, Fmoc-L-Glu(O-tBu)-OPfp, Fmoc-L-Phe-OPfp, Fmoc-Gly-OPfp, Fmoc-L-His(Boc)-QPfp, Fmoc-L-Ile-OPfp, Fmoc-L-Lys(Boc)-OPfp, Fmoc-L-Leu-OPfp, Fmoc-L-Met-OPfp, Fmoc-L-Asn-OPfp, Fmoc-L-Pro-OPfp, Fmoc-L-Gln-OPfp, Fmoc-L-Arg(Mtr)-OPfp, Fmoc-L-Ser(t-Bu)-ODhbt, Fmoc-L-Thr(t-Bu)-ODhbt, Fmoc-L-Val-OPfp, and Fmoc-L-Tyr-OPfp.

The protected amino acids were placed in microtiter plate wells with HOBt, and the pin block placed over the plate, immersing the pins in the wells. The assembly was then sealed in a plastic bag and allowed to react at 25° C. for 18 hours to couple the first amino acids to the pins. The block was then removed, and the pins washed with DMF (2 min), MeOH (4×2 min), and again with DMF (2 min) to clean and deprotect the bound amino acids. The procedure was repeated for each additional amino acid coupled, until all octamers had been prepared. The free N-termini were then acetylated to compensate for the free amide, as most of the epitopes are not found at the N-terminus and thus would not have the associated positive charge. Acetylation was accomplished by filling the wells of a microtiter plate with DMF/acetic anhydride/triethylamine (5:2:1 v/v/v) and allowing the pins to react in the wells for 90 min at 20° C. The pins were then washed with DMF (2 min) and MeOH (4×2 min), and air dried for at least 10 min.

The side chain protecting groups were removed by treating the pins with tri-fluoroacetic acid/phenol/dithioethane (95:2.5:2.5, v/v/v) in polypropylene bags for 4 hours at room temperature. The pins were then washed in dichloromethane (2×2 min), 5% di-isopropylethylamine/dichloromethane (2×5 min), dichloromethane (5 min), and air-dried for at least 10 min. The pins were then washed in water (2 min), MeOH (18 hours), dried in vacuo, and stored in sealed plastic bags over silica gel.

Binding Assay

In order to assay binding to peptides, octamer-bearing pins prepared as described above were first treated by sonicating for 30 min in a disruption buffer (1% sodium dodecylsulfate, 0.1% 2-mercaptoethanol, 0.1 M NaH$_2$PO) at 60° C. The pins were then immersed several times in water (60° C.), followed by boiling MeOH (2 min), and allowed to air dry.

The pins were then precoated for 1 hour at 25° C. in microtiter wells containing 200 μL blocking buffer (1% ovalbumin, 1% BSA, 0.1% Tween® 80 (sorbitan monooleate), and 0.05% NaN$_3$ in PBS), with agitation. The pins were then immersed in microtiter wells containing two preparations of IgG obtained from sheep immunized with E2HV peptide.

Preparation of IgG Containing anti-HCV HV E2 Antibodies

The preparation of sheep IgG and of the conjugated peptide was as follows.

The sheep were immunized with 50 to 100 nmoles of the conjugated peptide in Freund's Complete Adjuvant (CFA); 14 days later, the sheep were immunized a second time, but the conjugated peptide was in Freund's incomplete adjuvant. Three to four weeks later, the sheep were bled, and IgG in the serum was precipitated with 50% ammonium sulfate. The precipitate was collected and treated with a solution containing 1% Triton® X-100 (octylphenoxy polyethoxy) ethanol (EO-9-10))., and 0.3% tri-N-butyl phosphate (TNBP). After the treatment, detergent was removed by precipitating the IgG fraction with 50% ammonium sulfate, collecting and washing the precipitate twice with a solution containing 50% ammonium sulfate, followed by solubilization in and dialysis for two days against phosphate buffered saline (PBS). The resulting IgG preparation was sterilized by passage through a filter prior to use for immunization.

Coupling of the Diphtheria Toxoid Carrier Protein to MCS

The peptide-diphtheria toxoid conjugates were prepared using the following protocol.

Materials:

ethylene diamine tetra-acetic acid (EDTA Na$_2$.2H$_2$O) (MW 372)

6-maleimido-caproic acid N-hydroxysuccinimide ester (MCS) (Sigma)-95% pure sodium dihydrogen orthophosphate (NaH$_2$PO$_4$)

nitrogen dimethylformamide (DMF)

Milli Q water 0.1 M phosphate buffer containing 5 mM EDTA, pH 6.66

0.1 M phosphate buffer, pH 8.0

0.1 M phosphate buffer, pH 7.0 sodium succinate [(CH$_2$COONa)$_2$.6H$_2$O]

cysteine hydrochloric acid (2% solution)

0.1 M sodium succinate/0.1 EDTA, pH 5.6

Purified diphtheria toxoid (Commonwealth Serum Laboratories, Victoria, Australia) was coupled to MCS according to the method described by Lee et al., (1980) *Mol. Immunol.* 17:749; Partis et al., (1983) *Prot. Chem.* 2:263; Peeters et al., (1989) *J. Immunol. Methods* 120:133; Jones et al., (1989) *J. Immunol. Methods* 123:211. 100 ml of diphtheria toxoid was passed through a G25 Sephadex column (17 cm×4 cm) to remove thiomersal. The toxoid was eluted with 0.1 M phosphate buffer pH 7.0 and the protein content of the eluate was assayed using the BCA protein determination (Pierce). The resulting solution was concentrated using an Amicon ultrafiltration unit to a final concentration of 10 mg/ml.

One milliliter of the toxoid solution was dialyzed with 0.1 M phosphate buffer, pH 8.0, and then mixed with a solution of 1.5 mg MCS in 200 μl DMF. The resulting solution was incubated at room temperature for 1 hour in the dark with occasional mixing. In order to separate the uncoupled MCS from the MCS-toxoid, the solution was passed through Sephadex® PD-10 (beaded gel dextran cross-linked with epichlorohydrin) column which had been equilibrated with 0.1 M phosphate buffer, pH 6.66 and the protein fraction was collected.

The number of maleimido groups coupled per carrier molecule was determined prior to coupling of the HCV peptides thereto. Thirty milliliters of the succinate/EDTA buffer was sparged with nitrogen for 2 minutes. Five milligrams of cysteine was transferred into a 25 ml volumetric flask and dissolved in a final volume of 25 ml of the sparged buffer. Aliquots of the solutions shown in Table 3 were transferred in duplicate to 25 ml screw capped bottles. Using separate pipettes, nitrogen was bubbled into each aliquot. Each bottle was then sealed and incubated at room temperature in the dark for 40 minutes with occasional swirling.

TABLE 3

| Solution | Sample (ml) | Standard (ml) | Blank (ml) |
|---|---|---|---|
| activated carrier | 0.3 | — | — |
| phosphate buffer | — | 0.3 | 0.3 |
| cysteine solution | 1.0 | 1.0 | — |
| succinate buffer | — | — | 1.0 |

*A 0.1 ml aliquot of each of the 3 solution was taken for an Ellman's determination.

Ellman's Test for the Quantitative Determination of Sulfhydryl

Materials Required:

Phosphate buffer, pH 8.0

Dissolve 15.6 g $NaH_2PO_4$ or 12.0 g $NaH_2PO_4$ anhydrous in approximately 700 ml Milli Q® water. Adjust the pH to 8.0 using 50% NaOH. Add Milli Q® water for a final volume of 1000 ml and then adjust the pH if necessary.

Ellman's Reagent

Dissolve 10.0 mg of 5,5'-dithiobis-2-nitrobenzoic acid (DTNB) in 2.5 ml of phosphate buffer, pH 8.0

0.1 ml of Ellman's reagent was added to each of the 0.1 ml aliquots of the solutions prepared above, namely the sample, standard and bland solutions. Five milliliters of phosphate buffer, pH 8.0, was then added to each aliquot, mixed well and allowed to stand for 15 minutes. The absorbance of each aliquot was measured in a 1 cm path length cell at 412 nm.

The number of maleimido groups present on the carrier protein was determined according to the following method. A 0.01 μmol per ml solution of —SH produces an absorbance of 0.136 in a 1 cm light path at 412 nm. The absorbance of the Standard or Sample (A) is equal to the amount of cysteine reacted with the coupled maleimido groups on the activated carrier protein. Since 1 mol of available —SH reacts with 1 mol of maleimido, the concentration in μmols of the maleimido groups present in the aliquot tested is equal to A(0.01)/0.136 mmol/ml. The total volume of the solution was 5.2 ml. Therefore, the total number of μmols present was equal to A(0.01)(5.2)/0.136. The sample solution had a total volume of 1.3 ml, of which 0.3 ml consisted of the activated carrier protein. The amount of maleimido groups present in the sample solution was calculated as A(0.01)(5.2)(1.3)/(0.136)(0.1)(0.3)=A(16.57) μmol/ml.

The MCS-activated carrier protein was stored at −20° C.

Reduction of the HCV Peptides

Prior to coupling of the HCV peptides to the MCS-activated carrier protein, the peptides were reduced to ensure that thiol groups present on the peptides were in the fully reduced —SH form.

Materials Required:

dithiothreitol (DTT)

ammonium hydrogen carbonate ($NH_4HCO_3$)

methanol

SEP-PAKs® (C18 cartridge, Waters), 1 cartridge for each 8 mg of peptide 0.1 M ammonium hydrogen carbonate buffer Dissolve 7.9 g $NH_4HCO_3$ in 1 L Milli Q® water Buffer A, 0.1% v/v trifluoroacetic acid (TFA) in Milli Q® water Buffer B, 60% v/v acetonitrile, 0.1% v/v TFA in Milli Q® water 15 mg of the HCV peptide were added to 2.5 ml of 0.1 M ammonium hydrogen carbonate containing a 10 fold molar excess of DTT. The resulting solution was mixed until the peptide had dissolved and was then allowed to stand for 1 hour at room temperature. A pair of SEP-PAKs® were connected in series and activated by passing approximately 20 ml of methanol and then 20 ml of Buffer A through the pair of SEP-PAKs®. The peptide/DTT sample was slowly passed through a pair of SEP-PAKs®. The DTT was eluted with approximately 20 ml of Buffer A. The reduced peptide was eluted with 7 ml of Buffer B into a pre-weighed bottle and then freeze-dried overnight. The bottles were then weighed to determined the amount of recovered peptide. The reduced peptide was then immediately coupled to the MCS-activated carrier protein.

Coupling HCV Peptides to MCS-Activated Carrier Protein

Approximately 100 ml of 0.1 M phosphate buffer with 5 mM EDTA, pH 6.66 was degassed under vacuum and then sparged with nitrogen for 10 minutes. Twenty milliliters of a 10 mg/ml solution of the MCS-activated carrier protein was carefully sparged with nitrogen to prevent excessive frothing. 5 mg of the reduced peptide were dissolved in approximately 0.2 ml of the degassed sparged phosphate/EDTA buffer, pH 6.66 and then mixed with the MCS-activated carrier protein solution. The resulting mixture was transferred into a screw capped bottle which was then filled with nitrogen and sealed. The solution was further degassed by holding the bottle in a Branson 2000® sonication bath for 2 minutes. The bottle was covered with aluminum foil and incubated overnight at room temperature with slow mixing on a shaker table.

The resultant conjugate was soluble and the uncoupled peptide was removed by passing the mixture over a Sephadex® PD-10 (beaded gel dextran cross-linked with epichlorohydrin) column which had been equilibrated with the phosphate/EDTA buffer, pH 6.66. The protein fraction was collected. The amount of peptide conjugated to the carrier protein was determined by amino acid analysis.

An amino acid analysis of 150 µl aliquots of both the conjugate and the carrier protein was performed. The average ratio of the level of amino acids contributed solely by the carrier protein was determined to calculate the amount of conjugated peptide produced. Levels of serine, threonine, tryptophan, methionine, tyrosine and cysteine were not determined as these amino acids are modified under the standard hydrolysis conditions.

Example 3

Passive Immunization with Anti-E2HV Antibodies

The IgG preparation from sheep immunized with a 30-mer peptide from E2HV of HCV1 was used for passive immunization to determine its protective effect against infection by HCV.

A chimpanzee was immunized with the anti-E2HV sheep IgG preparation that had been prepared from sheep immunized with a peptide encompassing HCV1 E2HV coupled to diphtheria toxoid. The preparation of the IgG preparation is described in Example 2. Twenty four hours later, the chimpanzee was challenged with 10 chimpanzee infectious doses (CID)/ml of HCV1 inocula. Prior to inoculation, the virus was thawed, immediately diluted to $10^{-5}$ in sheep serum, and incubated for 20 minutes at room temperature.

The chimpanzee was examined for signs of viremia at weekly intervals after the challenge, using as indicators physical symptomology associated with HCV infection and the presence of viral RNA in the serum as detected by PCR assay. Using the PCR assay method described below, HCV RNA was still not detected in the serum after 6 weeks post-challenge. In chimpanzees viral RNA is usually detected approximately three weeks after the challenge dose. The lack of physical symptoms associated with acute viremia and the absence of histological and biochemical markers associated with HCV infections were consistent with the results of the PCR HCV-RNA assays. These results are suggestive that the passively immunized animals did not become infected by the viral challenge.

The following protocols are used in this study.

Detection of HCV Viral RNA

The following method is employed to detect viral RN-A circulating in plasma or present in liver biopsy tissue collected from the chimpanzees. Commencing one week following the viral challenge, the chimpanzee is monitored for viremia on a weekly basis. In order to detect viremia, blood samples and liver biopsy specimens are collected on a weekly basis. Tissue collected by liver biopsy is examined histologically for signs of necrosis and/or inflammation. In addition, hepatocytes from the biopsy material are examined by electron microscopy for the presence of tubules characteristic of HCV infection. The blood samples are also analyzed by an ELISA assay for the presence of antibodies to segments of viral polypeptides which were not utilized in preparing the vaccine.

cPCR Method to Detect HCV RNA in Liver and in Serum

In the cPCR assay, putative viral RNA in the sample is reverse transcribed into cDNA with reverse transcriptase; a segment of the resulting cDNA is then amplified utilizing a modified version of the PCR technique described by Saiki et al. (1986). The primers for the cPCR technique are derived from HCV RNA. Amplified product corresponding to the HCV-RNA is detected utilizing a probe derived from HCV cDNA.

The cPCR/HCV assay used in these studies was performed utilizing the following methods for the preparation of RNA, the reverse transcription of the RNA into cDNA, the amplification of specific segments of the cDNA by PCR, and the analysis of the PCR products.

In order to isolate total RNA from plasma, the plasma was diluted five- to ten-fold with TENB (0.1 M NaCl, 50 mM Tris-HCl, pH 8.0, 1 mM EDTA) and incubated in a Proteinase K/SDS solution (0.5% SDS, 1 mg/ml Proteinase K, 20 micrograms/ml Poly A carrier) for 60 to 90 minutes at 37° C. The samples were extracted once with phenol (pH 6.5), the resulting organic phase was re-extracted once with TENB containing 0.1% SDS, and the aqueous phases of both extractions were pooled and extracted twice with an equal volume of phenol/$CHCl_3$/isoamyl alcohol [1:1(99:1)]. The resulting aqueous phases were extracted with an equal volume of $CHCl_3$/isoamyl alcohol (99:1) twice, and ethanol precipitated using 0.2 M sodium acetate, pH 6.5, and 2.5 volumes of 100% ethanol; precipitation was overnight at −20° C.

The cDNA used as a template for the PCR reaction was prepared utilizing the designated samples for preparation of the corresponding cDNAs. Each RNA sample (containing RNA from 40 microliters of plasma) was incubated in a 25 microliter reaction containing 100 pmol micromolar of JH51 primer, 1 millimolar of each deoxyribonucleotide triphosphate (dNTP), 50 millimolar Tris-HCL, pH 8.3, 5 millimolar $MgCl_2$, 5 millimolar dithiothreitol (DTT), 73 millimolar KCl, 40 units of RNase inhibitor (RNASIN), and 5 units of AMV reverse transcriptase. The incubation was for 60 minutes at 37° C. Following cDNA synthesis, the reactions were diluted with 50 microliters of deionized water (DIW), boiled for 10 minutes, and cooled on ice.

Amplification of a segment of the HCV cDNA was performed utilizing two synthetic oligomer 18-mer primers whose sequences were derived from HCV cDNA clones JHC51 (anti-sense) and JHC93B (sense). The primers were used at a final concentration of 100 pmol/µl each. In order to amplify the segment of HCV cDNA which is flanked by the primers, the cDNA samples were incubated with 0.1 microgram of RNAse A and the PCR reactants of the Perkin Elmer Cetus PCR kit (N801-0043 or N801-0055) according to the manufacturer's instructions. The PCR reaction was performed for 40 cycles in a Perkin Elmer Cetus DNA thermal cycler model 9600. Each cycle consisted of a 10 second denaturation step at 94° C., and annealing step of 30 seconds at 55° C., and an extension step of 3 minutes at 72° C. However, the annealing step in the final cycle 40 was 7 minutes rather than 30 seconds. After amplification the samples were analyzed using a liquid hybridization protocol described in Weiner, A. J. et al., "PCR: Application to Hepatitis C virus (HCV) Research and Diagnostics" in Frontiers in Virology Vol. 1 (Springer Verlag).

The expected PCR product was 242 bp in size. Products which hybridized with the radiolabeled probe and migrated in the gels in this size range were scored as positive for viral RNA.

Liquid Hybridization Protocol for Analysis of HCV PCR Products

10× salts:

| 5 ml | 20 × SSC |
|---|---|
| 40 ml | 250 mM EDTA |
| 55 ml | P-30 DIW (good quality "injectable" water) |
| ... | ... |
| 100 ml | 1 × SSC, 10 mM EDTA |

Post-PCR reaction:
  Remove samples from under oil (PCR tube) to fresh tubes (screw-capped), avoiding the oil. Aliquot 10 µl to fresh tube for hybridization reaction.

Probe mix/reaction:

| 7 µl P-30 DIW: |
|---|
| 2 µl 10 × Salts: |
| 1 µl Alex 89 or 5'UTP-2: minimum of 2.5 $10^5$ cpm/µl (1 µl = 1 pmol). Use 1 pmol/reaction. |
| ... |
| 10 µl probe mix (enough for one hybridization reaction) |

Hybridization:
  combine 10 µl sample and 10 µl probe mix
  add 1 or 2 drops oil to cover
  heat 100° C. 5' in heat block (VWR)
  remove block from heater to bench top
  cool to ~55° C. (20–30')
  remove samples from under oil to tubes with 2 µl 10× dye
  run total or ½ on 6% PAG (BioRad Mini-Protean II system)
  attach gel to 3 MM paper and cover with Saran wrap
  dry 20' (till flat) on gel dryer
  Autoradiograph by exposing film to gel 3 hours, overnight, and 5 to 7 days.

10× dye:
  0.25% Bromophenol Blue
  0.25% Xylenecyanol FF (XCFF)
  25% Ficoll type 400 in $H_2O$
  (from Maniatis)

Gels: Use either precast 5% TBE gels (BioRad) or pour 6% TBE gels.
  6% TBE PAG:
  8 ml 30–0.8% Acrylamide
  4 ml 10× TBE
  28 ml P-30 DIW
  de-gas with vacuum
  add 240 µl 10% APS
  add 40 µl TEMED
  swirl and pour, set 20'

Note: Samples can be ethanol-precipitated in order to use 100% of the PCR products in the hybridization.

Example 4

Binding of Anti-thyroxin Monoclonal Antibodies to HCV E2HV Domain Peptides

Figure 6:
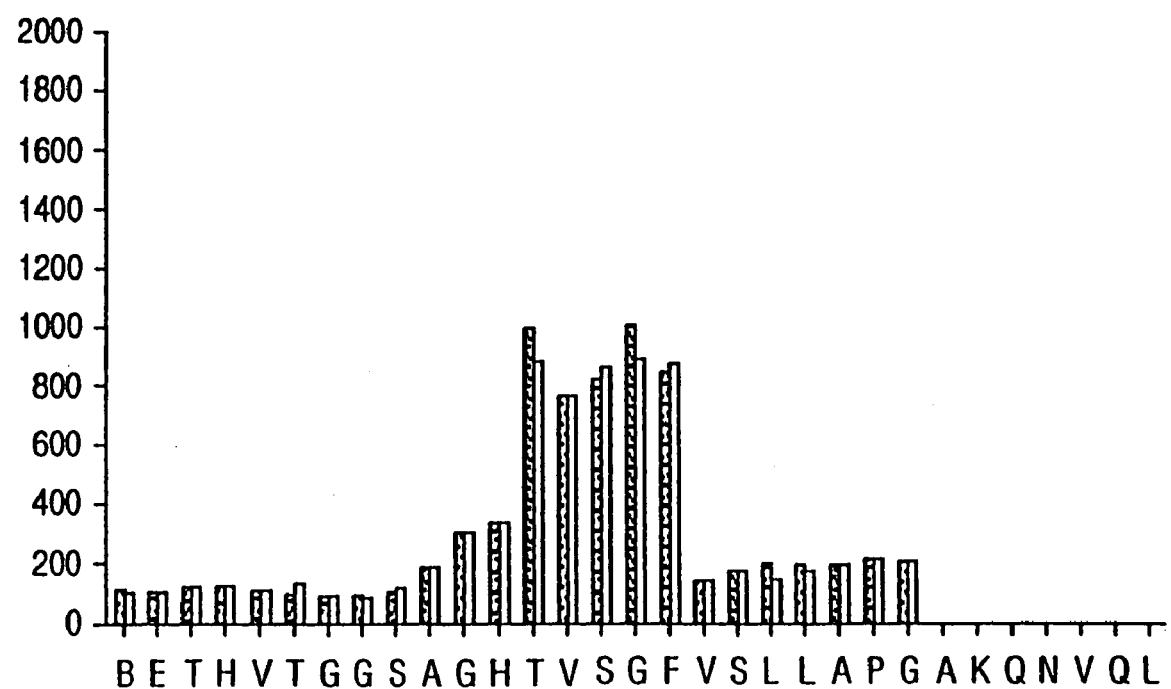
FIG. 6 (SEQ. ID. NO. 133) presents bar graphs of epitope mapping showing the binding of monoclonal anti-thyroxin antibodies to overlapping peptides of the E2HV region. The SEQ ID NO for the sequence recited is SEQ ID NO: 133.

Monoclonal antibodies that bind to thyroxine (T4) were prepared by Dr. Mario Geysen, Chiron Mimitopes Ltd, Australia. The binding of these antibodies to overlapping peptides that span the E2HV region was assessed. Peptides on pins were prepared essentially as described above in Example 2, except that the HCV E2HV sequence spanned from amino acid 383 to 413 of HCV1. The binding of the anti-T4 monoclonal antibodies to the HCV E2HV mimitopes was performed in duplicate. The binding results are shown in the bar graph in FIG. 6, where the solid and shaded bars represent binding of each of the duplicate samples. As seen in the figures, the anti-T4 antibodies were immunologically reactive with epitope(s) encompassed within the HCV1 sequence that spanned from aa395 to aa407.

Example 5

Binding of Serum Proteins to HCV

The binding of three serum proteins, human prealbumin, human serum albumin, and thyroid binding globulin (TBG) to overlapping peptides spanning E2HV was performed. Octamer bearing pins were prepared as described in Example 1. The binding of the designated serum proteins to the octamers was determined by an ELISA assay, using antibodies directed to the specific proteins. Controls were run in the absence of the serum proteins but in the presence of the respective antibodies. The results, shown as difference plots, are shown in FIGS. 7A–7C. Based upon the results, it appears that transthyretin binds to at least one minimum epitope in the hypervariable region. In addition, the results are suggestive that TBG binds to two minimum epitopes, one of which encompasses the SLF-G (SEQ. ID. NO: 134) motif.

What is claimed is:

1. An immunogenic polypeptide comprising an HCV immunogen, wherein said HCV immunogen comprises the amino acid sequence Xaa-Thr-Xaa-Val-Thr-Gly-Gly-Xaa-Ala-Ala-Arg-Thr-Thr-Xaa-Gly-Xaa-Xaa-Ser-Leu-Phe-Xaa-Xaa-Gly-Xaa-Ser-Gln-Xaa-Ile-Gln-Leu-Ile (SEQ ID NO:8).

2. The immunogenic polypeptide of claim 1, wherein the immunogenic polypeptide is coupled to a diphtheria toxoid.

3. The immunogenic polypeptide of claim 1, wherein said immunogenic polypeptide consists of the amino acid sequence of SEQ ID NO:8.

4. The immunogenic polypeptide of claim 1, wherein said HCV immunogen is fused to a non-HCV amino acid sequence.

* * * * *